(12) United States Patent
Roll et al.

(10) Patent No.: US 10,034,735 B2
(45) Date of Patent: Jul. 31, 2018

(54) IMPLANTS, TOOLS, AND METHODS FOR TREATMENTS OF PELVIC CONDITIONS

(75) Inventors: Jessica L. Roll, Pheonix, AZ (US); James R. Mujwid, Edina, MN (US); John E. Titus, Lonsdale, MN (US); Mark S. Bouchier, Lakeville, MN (US); Karl A. Jagger, Deephaven, MN (US); Jessica E. Felton, Minneapolis, MN (US); Scott L. Sjoquist, Minnetonka, MN (US); Danielle E. Steffens, Thorton, CO (US); James A. Alexander, Excelsior, MN (US); Randall P. Rowland, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 737 days.

(21) Appl. No.: 14/006,875

(22) PCT Filed: Feb. 28, 2012

(86) PCT No.: PCT/US2012/026888
§ 371 (c)(1),
(2), (4) Date: Apr. 14, 2014

(87) PCT Pub. No.: WO2012/134689
PCT Pub. Date: Oct. 4, 2012

(65) Prior Publication Data
US 2015/0305847 A1   Oct. 29, 2015

Related U.S. Application Data

(60) Provisional application No. 61/468,069, filed on Mar. 28, 2011, provisional application No. 61/484,062, filed on May 9, 2011.

(51) Int. Cl.
*A61F 2/00* (2006.01)

(52) U.S. Cl.
CPC .......... *A61F 2/0063* (2013.01); *A61F 2/0045* (2013.01); *A61F 2002/0072* (2013.01);
(Continued)

(58) Field of Classification Search
CPC ............ A61F 2/0045; A61F 2250/0007; A61F 2/0063; A61F 2250/0097;
(Continued)

(56) References Cited

U.S. PATENT DOCUMENTS

| 3,124,136 A | 3/1964 | Usher |
| 3,384,073 A | 5/1968 | Van Winkle, Jr. |

(Continued)

FOREIGN PATENT DOCUMENTS

| AU | 2002241673 | 11/2005 |
| CA | 2404459 | 8/2005 |

(Continued)

OTHER PUBLICATIONS

Araki, Tohru, et. al., "The Loop-Loosening Procedure for Urination Difficulties After Stamey Suspension of the Vesical Neck," J. of Urology, vol. 144, Aug. 1990, pp. 319-323.

(Continued)

*Primary Examiner* — Navin Natnithithadha
*Assistant Examiner* — Sunita Reddy
(74) *Attorney, Agent, or Firm* — Brake Hughes Bellermann LLP

(57) ABSTRACT

Described are devices, systems, and combinations useful for monitoring tension in an implant, which may be an implant useful to treat a pelvic condition, the device, system, or combination including an implant and a tension indicator.

18 Claims, 29 Drawing Sheets

(52) U.S. Cl.
CPC . *A61F 2220/0033* (2013.01); *A61F 2250/006* (2013.01); *A61F 2250/0007* (2013.01); *A61F 2250/0012* (2013.01); *A61F 2250/0097* (2013.01)

(58) Field of Classification Search
CPC ........ A61F 2220/0033; A61F 2250/006; A61F 2002/0072; A61F 2250/0012
USPC .................. 600/29, 30, 37; 128/897–899
See application file for complete search history.

(56) References Cited

U.S. PATENT DOCUMENTS

| | | |
|---|---|---|
| 3,613,679 A | 10/1971 | Bijou |
| 4,865,031 A | 9/1989 | O'Keeffe |
| 4,920,986 A | 5/1990 | Biswas |
| 4,932,962 A | 6/1990 | Yoon et al. |
| 5,007,894 A | 4/1991 | Enhorning |
| 5,019,032 A | 5/1991 | Robertson |
| 5,112,344 A | 5/1992 | Petros |
| 5,123,428 A | 6/1992 | Schwarz |
| 5,328,077 A | 7/1994 | Lou |
| 5,362,294 A | 11/1994 | Seitzinger |
| 5,376,097 A | 12/1994 | Phillips |
| 5,413,598 A | 5/1995 | Moreland |
| 5,527,342 A | 6/1996 | Pietrzak et al. |
| 5,562,689 A | 10/1996 | Green et al. |
| 5,582,188 A | 12/1996 | Benderev et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,697,931 A | 12/1997 | Thompson |
| 5,732,475 A | 3/1998 | Sacks et al. |
| 5,785,640 A | 7/1998 | Kresch et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,922,026 A | 7/1999 | Chin |
| 6,030,393 A | 2/2000 | Corlew |
| 6,039,686 A | 3/2000 | Kovac |
| 6,042,534 A | 3/2000 | Gellman et al. |
| 6,050,937 A | 4/2000 | Benderev |
| 6,053,935 A | 4/2000 | Brenneman et al. |
| 6,110,101 A | 8/2000 | Tihon et al. |
| 6,142,968 A | 11/2000 | Pigg et al. |
| 6,174,279 B1 | 1/2001 | Girard |
| 6,200,330 B1 | 3/2001 | Benderev et al. |
| 6,306,079 B1 | 10/2001 | Trabucco |
| 6,328,686 B1 | 12/2001 | Kovac |
| 6,334,446 B1 | 1/2002 | Beyar |
| 6,352,553 B1 | 3/2002 | van de Burg et al. |
| 6,382,214 B1 | 5/2002 | Raz et al. |
| 6,406,423 B1 | 6/2002 | Scetbon |
| 6,423,080 B1 | 7/2002 | Gellman et al. |
| 6,432,074 B1 * | 8/2002 | Ager ................ A61F 13/00059 602/75 |
| 6,451,024 B1 | 9/2002 | Thompson et al. |
| 6,482,214 B1 | 11/2002 | Sidor, Jr. et al. |
| 6,502,578 B2 | 1/2003 | Raz et al. |
| 6,582,443 B2 | 6/2003 | Cabak et al. |
| 6,599,323 B2 | 7/2003 | Melican et al. |
| 6,612,977 B2 | 9/2003 | Staskin |
| 6,638,284 B1 | 10/2003 | Rousseau et al. |
| 6,641,524 B2 | 11/2003 | Kovac |
| 6,641,525 B2 | 11/2003 | Rocheleau |
| 6,648,921 B2 | 11/2003 | Anderson |
| 6,682,475 B2 * | 1/2004 | Cox ................ A61F 2/2481 600/37 |
| 6,689,047 B2 | 2/2004 | Gellman et al. |
| 6,691,711 B2 | 2/2004 | Raz |
| 6,699,175 B2 | 3/2004 | Miller |
| 6,702,827 B1 | 3/2004 | Lund |
| 6,755,781 B2 | 6/2004 | Gellman |
| 6,802,807 B2 | 10/2004 | Anderson |
| 6,884,212 B2 | 4/2005 | Thierfelder et al. |
| 6,911,003 B2 | 6/2005 | Anderson et al. |
| 6,932,759 B2 | 8/2005 | Kammerer |
| 6,936,052 B2 | 8/2005 | Gellman et al. |
| 6,953,428 B2 | 10/2005 | Gellman et al. |
| 6,971,986 B2 | 12/2005 | Staskin et al. |
| 6,981,944 B2 | 1/2006 | Jamiolkowski |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,070,556 B2 | 7/2006 | Anderson et al. |
| 7,070,558 B2 | 7/2006 | Gellman et al. |
| 7,087,065 B2 | 8/2006 | Ulmsten et al. |
| 7,112,210 B2 | 9/2006 | Ulmsten et al. |
| 7,131,944 B2 | 11/2006 | Jaquetin |
| 7,229,404 B2 | 6/2007 | Bouffier |
| 7,229,453 B2 | 6/2007 | Anderson |
| 7,235,043 B2 | 6/2007 | Gellman et al. |
| 7,285,103 B2 | 10/2007 | Nathanson |
| 7,326,213 B2 | 2/2008 | Benderev et al. |
| 7,351,197 B2 | 4/2008 | Montpetit et al. |
| 7,364,541 B2 | 4/2008 | Chu et al. |
| 7,387,634 B2 | 6/2008 | Benderev |
| 7,393,320 B2 | 7/2008 | Montpetit et al. |
| 7,407,480 B2 | 8/2008 | Staskin et al. |
| 7,410,460 B2 | 8/2008 | Benderev |
| 7,413,540 B2 | 8/2008 | Gellman et al. |
| 7,422,557 B2 | 9/2008 | Arnal et al. |
| 7,442,557 B1 | 9/2008 | Arnal et al. |
| 7,500,945 B2 | 3/2009 | Cox et al. |
| 7,513,865 B2 | 4/2009 | Bourne et al. |
| 7,527,588 B2 | 5/2009 | Zaddem et al. |
| 7,601,118 B2 | 10/2009 | Smith et al. |
| 7,611,454 B2 | 11/2009 | De Leval |
| 7,621,864 B2 | 11/2009 | Suslian et al. |
| 7,637,860 B2 | 12/2009 | MacLean |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,766,926 B2 | 8/2010 | Bosely et al. |
| 7,981,024 B2 | 7/2011 | Levy |
| 2002/0147382 A1 | 10/2002 | Neisz et al. |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0010929 A1 | 1/2003 | Prieve et al. |
| 2003/0036676 A1 | 2/2003 | Scetbon |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0073235 A1 | 4/2004 | Lund |
| 2004/0225181 A1 | 11/2004 | Chu et al. |
| 2005/0000523 A1 | 1/2005 | Beraud |
| 2005/0004427 A1 | 1/2005 | Cervigni |
| 2005/0038451 A1 | 2/2005 | Rao et al. |
| 2005/0131391 A1 | 6/2005 | Chu et al. |
| 2005/0131393 A1 | 6/2005 | Chu et al. |
| 2005/0283189 A1 | 12/2005 | Rosenblatt et al. |
| 2006/0009673 A1 * | 1/2006 | Chan ................ A61F 2/0045 600/29 |
| 2006/0053903 A1 | 3/2006 | Berenyi et al. |
| 2006/0089524 A1 | 4/2006 | Chu |
| 2006/0089525 A1 | 4/2006 | Mamo et al. |
| 2006/0195007 A1 | 8/2006 | Anderson |
| 2006/0195011 A1 | 8/2006 | Arnal |
| 2006/0287571 A1 | 12/2006 | Gozzi et al. |
| 2007/0015957 A1 * | 1/2007 | Li ................ A61F 2/0045 600/37 |
| 2007/0021649 A1 * | 1/2007 | Nowlin ................ A61F 2/0045 600/30 |
| 2008/0039678 A1 | 2/2008 | Montpetit et al. |
| 2008/0072404 A1 | 3/2008 | Wetter |
| 2008/0140218 A1 | 6/2008 | Staskin et al. |

(56) References Cited

U.S. PATENT DOCUMENTS

| | | |
|---|---|---|
| 2008/0251002 A1 | 10/2008 | Burleigh |
| 2008/0300607 A1 | 12/2008 | Meade et al. |
| 2009/0221868 A1 | 9/2009 | Evans |
| 2009/0259092 A1 | 10/2009 | Ogdahl et al. |
| 2010/0256442 A1 | 10/2010 | Ogdahl et al. |
| 2010/0261950 A1 | 10/2010 | Lund |
| 2010/0261955 A1 | 10/2010 | O'Hern et al. |
| 2011/0034759 A1 | 2/2011 | Ogdahl et al. |
| 2011/0112357 A1 | 5/2011 | Chapman et al. |
| 2011/0124954 A1 | 5/2011 | Ogdahl |

FOREIGN PATENT DOCUMENTS

| | | |
|---|---|---|
| EP | 1060714 A3 | 9/2002 |
| WO | WO9317635 A1 | 9/1993 |
| WO | WO0057812 A1 | 10/2000 |
| WO | WO0106951 A1 | 2/2001 |
| WO | WO0139670 A1 | 6/2001 |
| WO | WO0156499 A1 | 8/2001 |
| WO | WO 02/028315 | 4/2002 |
| WO | WO02071953 A2 | 9/2002 |
| WO | WO0303778 A1 | 4/2003 |
| WO | WO03028585 A2 | 4/2003 |
| WO | WO03037215 A2 | 5/2003 |
| WO | WO03041613 A1 | 5/2003 |
| WO | WO2005122954 A1 | 12/2005 |
| WO | WO2007011341 A1 | 1/2007 |
| WO | WO 2007/016083 | 2/2007 |
| WO | WO2007027592 A2 | 3/2007 |
| WO | WO 2007/097994 | 8/2007 |
| WO | WO 2007/149348 | 12/2007 |
| WO | WO 2009/075800 | 6/2009 |
| WO | WO 2010/093421 | 8/2010 |
| WO | WO 2011/063412 | 5/2011 |
| WO | WO 2011/072148 | 6/2011 |

OTHER PUBLICATIONS

Asmussen et. al., "Simultaneous Urethro-Cystometry with a New Technique," Scand. J. Urol. Nephrol 10:7-11, 1976, pp. 7-10.

Beck et. al., "Treatment of Urinary Stress Incontinence with Anterior Colporrhapy," J. of Am. Col. of Obstetricians and Gynecologists, V.59, No. 3, Mar. 1982, pp. 269-.

Benderev, Theodore, "A Modified Percutaneous Outpatient Bladder Neck Suspension System," The J. of Urology, vol. 152, Dec. 1994, pp. 2316-2320.

Benderev, Theodore, "Anchor Fixation and Other Modifications of Endoscopic Bladder Neck Suspension," Urology, vol. 40, No. 5, Nov. 1992, pp. 409-419.

Blaivas et. al., "Pubovaginal Fascial Sling for the Treatment of Complicated Stress Urinary Incontinence," The J. of Urology, vol. 145, Jun. 1991, pp. 1214-1218.

Burch, John C., "Urethrovaginal fixation to Cooper's ligament for correction of stress incontinence, cystocele, and prolapse," Am. J. Obstetrics and Gynecology, vol. 31, No. 2, Feb. 1961.

DeLancey, John, "Structural support of the urethra as it relates to stress urinary incontinence: the hammock hypothesis," Am. J. Obstetrics and Gynecology, vol. 170, No. 6, Jun. 1994, pp. 1713-1723.

Enzelsberger et al., "Urodynamic and radiologic parameters before and after loop surgery for recurrent urinary stress incontinence," Acta. Obstet. Gynecol. Scand., 1990; 69:51-54.

Falconer et al., "Clinical outcome and changes in connective tissue metabolism after intravaginal slingplasty in stress incontinent women," Int. Urogynecol. J. (1996) 7:133-137.

Gilja et al., "A modifies raz bladder neck suspension operation (transvaginal burch)," The J. of Urology, vol. 153, 1455-1457, May 1995.

Hamilton et al., "Procedures for urinary incontinence in the United States, 1979-1997," Am. J. Obstet. Gynecol. vol. 189, No. 1, pp. 70-75 2003.

Hodgkinson et al., "Urinary stress incontinence in the female; III. Round-ligament technic for retropubic suspension of the urethra," Obstetrics & Gynecology, vol. 10, No. 5 (1957).

Ingelman-Sundberg, "Surgical treatment of female urinary stress incontinence," Contr. Gynec. Obstet., vol. 10 pp. 51-69 (1983).

Klutke et al., "The anatomy of stress incontinence: magnetic resonance imaging of the female bladder neck and urethra," The J. or Urology, vol. 149, pp. 563-567 (1990).

Klutke et al., "Instruments & Methods: transvaginal bladder neck suspension to cooper's ligament: a modified pereyra procedure," Obstetrics & Gynecology, vol. 88, No. 2, pp. 293-297 (1996).

Leach et al., "Female stress urinary incontinence clinical guidelines panel summary report on surgical management of female stress urinary incontinence," Am. Urological Assc., vol. 158, 875-880 (1997).

Loughlin et al., "Review of an 8-year experience with modifications of endoscopic suspension of the bladder neck for female stress urinary incontinence," The Journal of Urology, vol. 143, pp. 3-4 (1990).

O'Donnell, Pat, "Combined Raz urethral suspension and McGuire pubovaginal sling for treatment of complicated stress urinary incontinence," The J. of the Ark. Med. Society, vol. 88, No. 8, pp. 389-392 (1992).

Parra et al., "Experience with a simplified technique for the treatment of female stress urinary incontinence," British J. of Urology, vol. 68:615-617 (1990).

Pereyra, Armand, "A simplified surgical procedure for the correction of stress incontinence in women," West. J. Obst. & Gynec., Jul./Aug. 1959.

Petros et al., "The autogenic ligament procedure: a technique for planned formation of an artificial neo-ligament," Acta Obstet Gynecol Scand, 69 Suppl. 153:43-51 (1990)

Petros et al., "Cough transmission ratio: an indicator of suburethral vaginal wall tension rather than urethral closure?", Acta Obstet Gynecol Scand, 69 Suppl. 153:43-51 (1990).

Petros et al., "Non stress non urge female urinary incontinence—diagnosis and cure: a preliminary report," Acta Obstet Gynecol Scand, 69 Suppl. 153:69-70 (1990).

Petros et al., "Urethral pressure increase on effort originates from within the urethra, and continence from musculovaginal closure," Neurology and Urodynamics, 14:337-350 (1995).

Petros et al., "An analysis of rapid pad testing and the history for the diagnosis of stress incontinence," Acta Obstet Gynecol Scand, 71:529-536 (1992).

Petros et al., "An integral theory of female urinary incontinence," Acta Obstet Gynecol Scand, 69 Suppl. 153:7-31 (1990).

Petros et al., "Anchoring the midurethra restores bladder-beck anatomy and continence," The Lancet, vol. 354 (1999).

Petros et al., "The development of the intravaginal slingplasty procedure: IVS II (with bilateral tucks)," Scand. J. Urol. Nephrol. Suppl. No. 153:61-69 (1993).

Petros et al., "Part IV: Surgical applications of the theory—Development of the intravaginal sling plasty (IVS) procedure," Scand. J. Urol. Nephrol. Suppl. No. 153:53-57 (1993).

Petros et al., "An anatomical basis for success and failure of female incontinence surgery," Scand. J. Urol. Nephrol. Suppl. No. 153:55-61 (1993).

Petros et al., "Part II. The biomechanics of vaginal tissue and supporting ligaments with special relevance to the pathogenesis of female urinary incontinence," Scand. J. Urol. Nephrol. Suppl. No. 153:29-31 (1993).

Petros et al., "Further development of the intravaginal slingplasty procedure—IVS III (with midline tuck)," Scand. J. Urol. Nephrol. Suppl. No. 153:69-73 (1993).

Petros et al., "Part III. Surgical principles deriving from the theory," Scand. J. Urol. Nephrol. Suppl. No. 153:41-53 (1993).

Raz et al., "The Raz bladder neck suspension: results in 206 patients," The Journal of Urology, pp. 845-846 (1992).

Raz et al., "Modified bladder neck suspension for female stress incontinence," Urology, vol. XVII, No. 1, pp. 82-86 (1981).

Seim et al., "A study of female urinary incontinence in general practice," Scand J. Urol. Nephrol 30;465-471 (1996).

(56) References Cited

OTHER PUBLICATIONS

Sloan et al., "Stress incontinence of urine: a retrospective study of the complications and late results of simple suprapubic suburethral fascial slings," The Journal of Urology, vol. 110, pp. 533-537 (1953).

Stanton, Stuart, "Suprapubic approaches for stress incontinence in women," JAGS 38;348-351 (1990).

Ulmsten et al., "The unstable female urethra," Am. J. Obstet & Gynecol. vol. 144, No. 1 (1982).

Ulmsten et al., "Different biochemical composition of connective tissue in continent and stress incontinent women," Acta Obstet. Gynecol. Scand. 66:455-457 (1987).

Ulmsten et al., "Female urinary incontinence—a symptom, not a urodynamic disease. Some theoretical and practical aspect of the diagnosis a treatment of female urinary incontinence," Int. Urogynecology J. 6:2-3 (1995).

Ulmsten et al., "An ambulatory surgical procedure under local anesthesia for treatment of female urinary incontinence," Int. Urogynecology J. 7:81-86 (1996).

Ulmsten et al., "A multicenter study of tension-free vaginal tape (TVT) for surgical treatment of stress urinary incontinence," Int. Urogynecology J. 9:210-213 (1998).

Waxman et al., "Advanced urologic surgery for urinary incontinence," The female Patient, vol. 21, pp. 93-101 (1996).

Webster, George, "Female Urinary Incontinence," Urologic Surgery, $3^{rd}$ Ed., pp. 665-680 (1983).

Zacharin, Robert, "The suspensory mechanism of the female urethra," Journal of Anatomy, vol. 97, Part 3, pp. 423-430 (1963).

Third Examination Report for Australian Application No. 2012238105, dated Feb. 28, 2017, 5 pages.

Aldridge, "Transplantation of Fascia for Relief of Urinary Stress Incontinence", American Journal of Obstetrics and Gynecology, vol. 44, 1948, pp. 398-411.

Blaivas, "Commentary: Pubovaginal Sling Procedure", Experience with Pubovaginal Slings, Surgery for Female Urinary Incontinence, 1990, pp. 93-101.

Blaivas, et al., "Type III Stress Urinary Incontinence: Importance of Proper Diagnosis and Treatment", Surgical Forum, Gynecology and Obstetrics, 1984, pp. 473-475.

Boston Scientific, "Surgical Mesh Sling Kit", Advantage AT™, 2002, 6 pages.

Bryans, "Marlex Gauze Hammock Sling Operation With Cooper's Ligament Attachment in the Management of Recurrent Urinary Stress Incontinence", American Journal of Obstetrics and Gynecology, vol. 133, No. 3, Feb. 1979, pp. 292-294.

Mascio, "Therapy of Urinary Stress Incontinence in Women Using Mitek® GII Anchors", Mitek® Brochure, 1993, 5 pages.

Petros, "Medium-term Follow-up of the Intravaginal Slingplasty Operation Indicates Minimal Deterioration of Urinary Continence with Time", Aust NZ J Obstet Gynaecol, vol. 39, No. 3, Aug. 1999, pp. 354-356.

Petros, "New Ambulatory Surgical Methods Using an Anatomical Classification of Urinary Dysfunction Improve Stress Urge and Abnormal Emptying", Urogynecology Journal, Pelvic Floor Dysfunction, vol. 8, 1997, pp. 270-278.

Stanton, et al., "Surgery of Female Incontinence", Second Edition, Chapter 7, 1986, pp. 105-113.

* cited by examiner

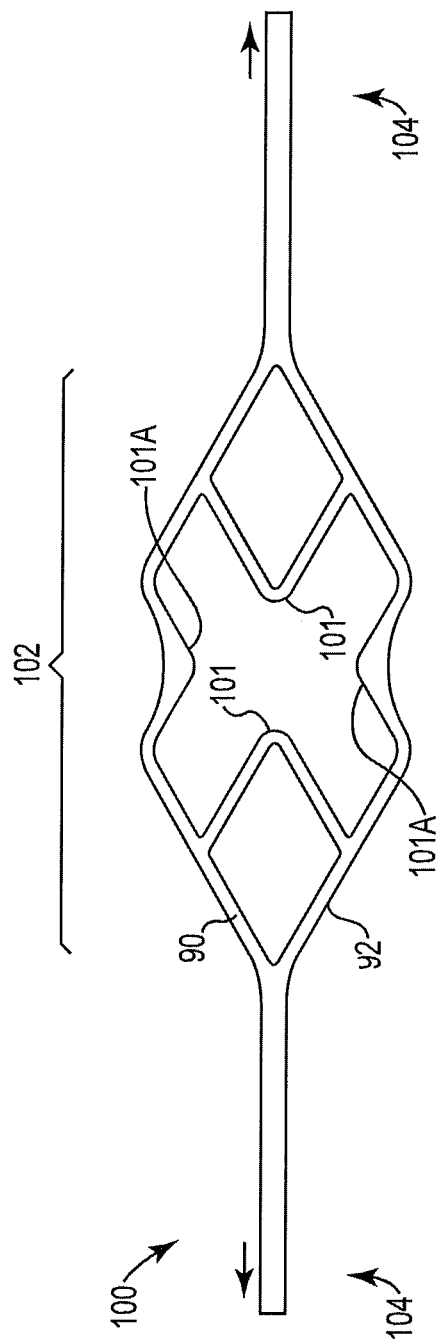

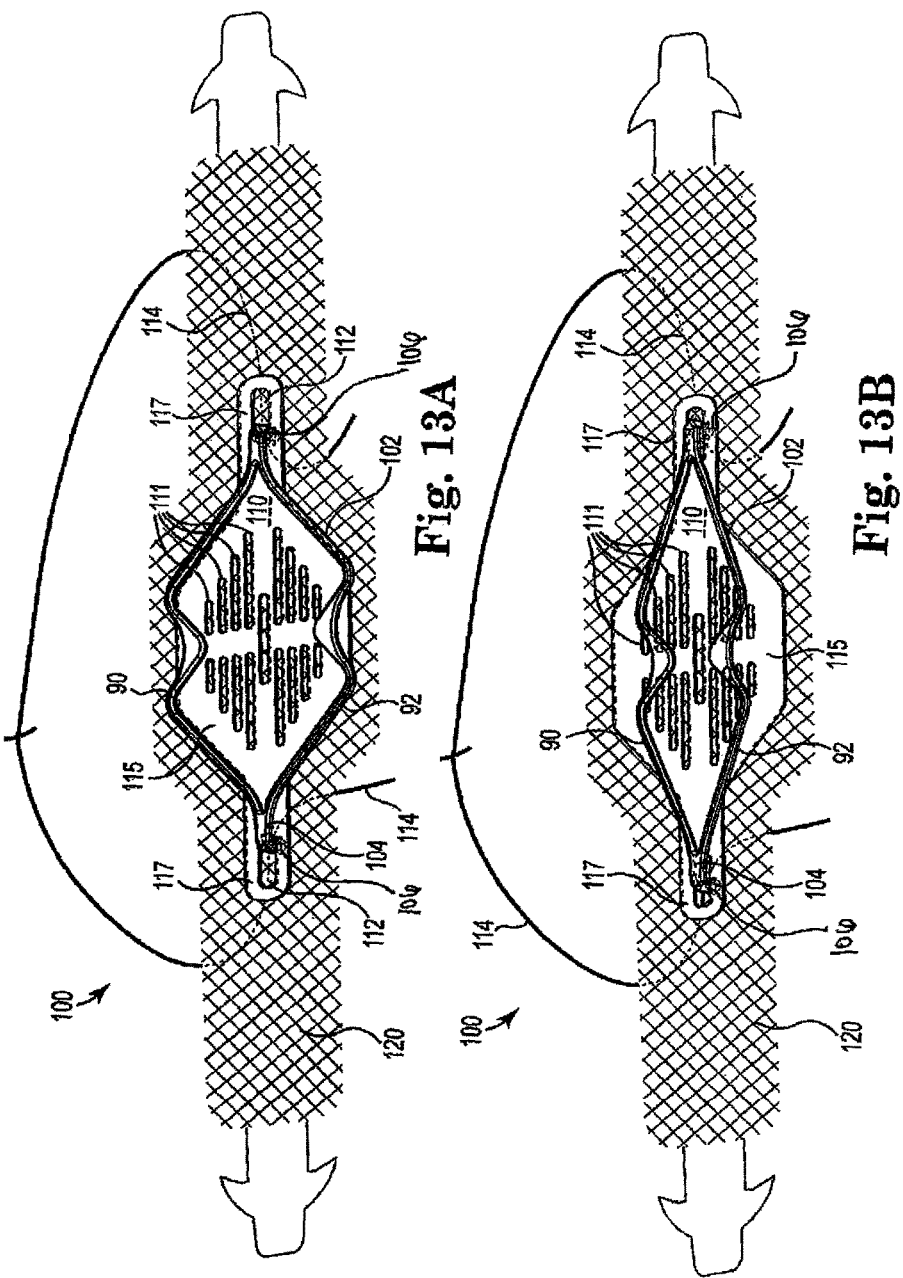

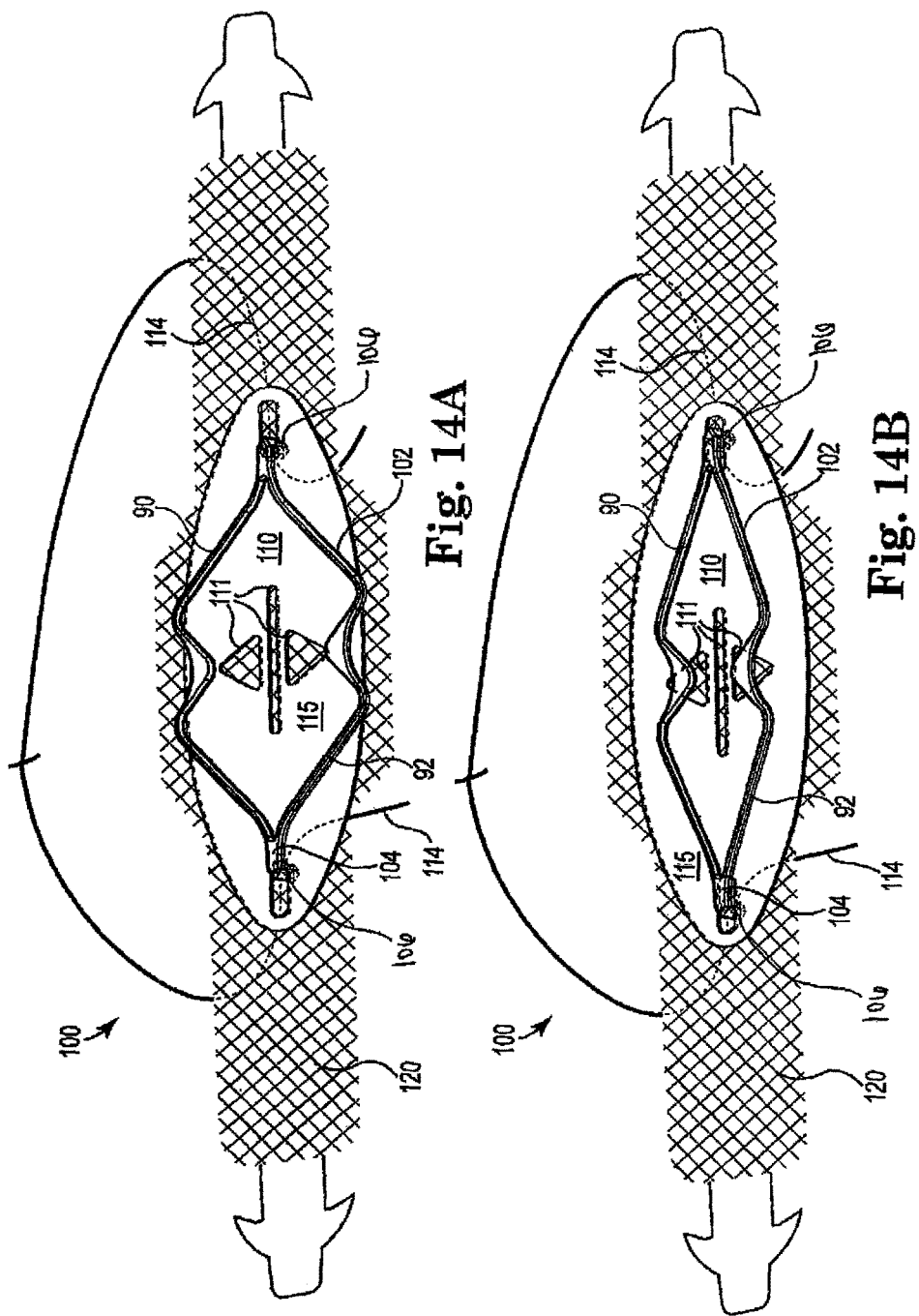

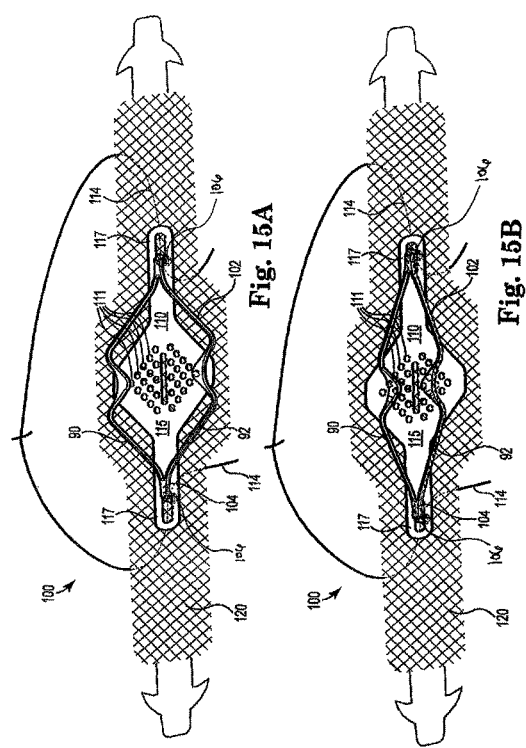

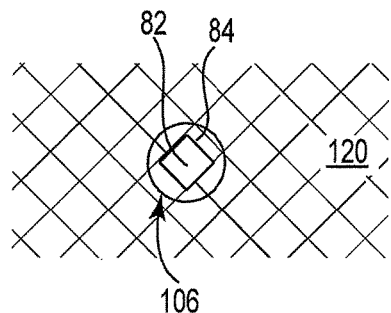
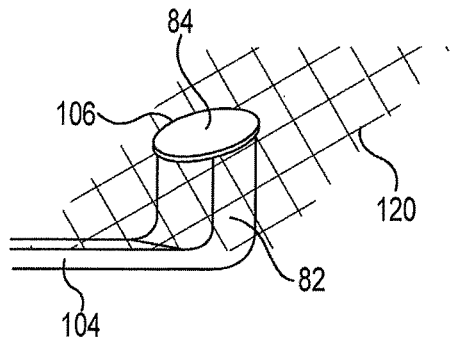
Fig. 17A       Fig. 17B
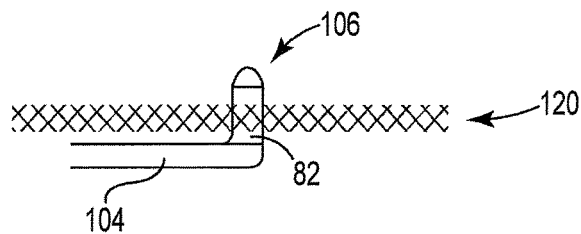
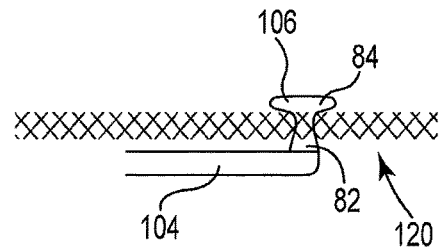
Fig. 17C       Fig. 17D
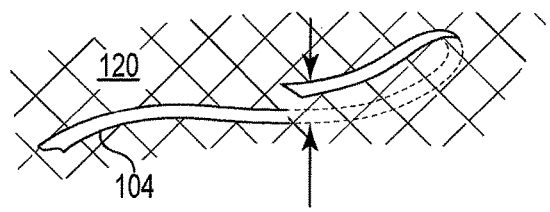
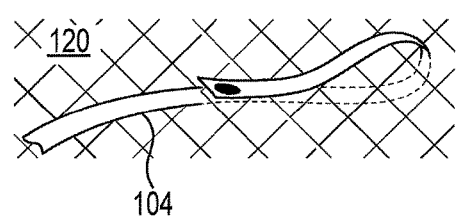
Fig. 17E       Fig. 17F

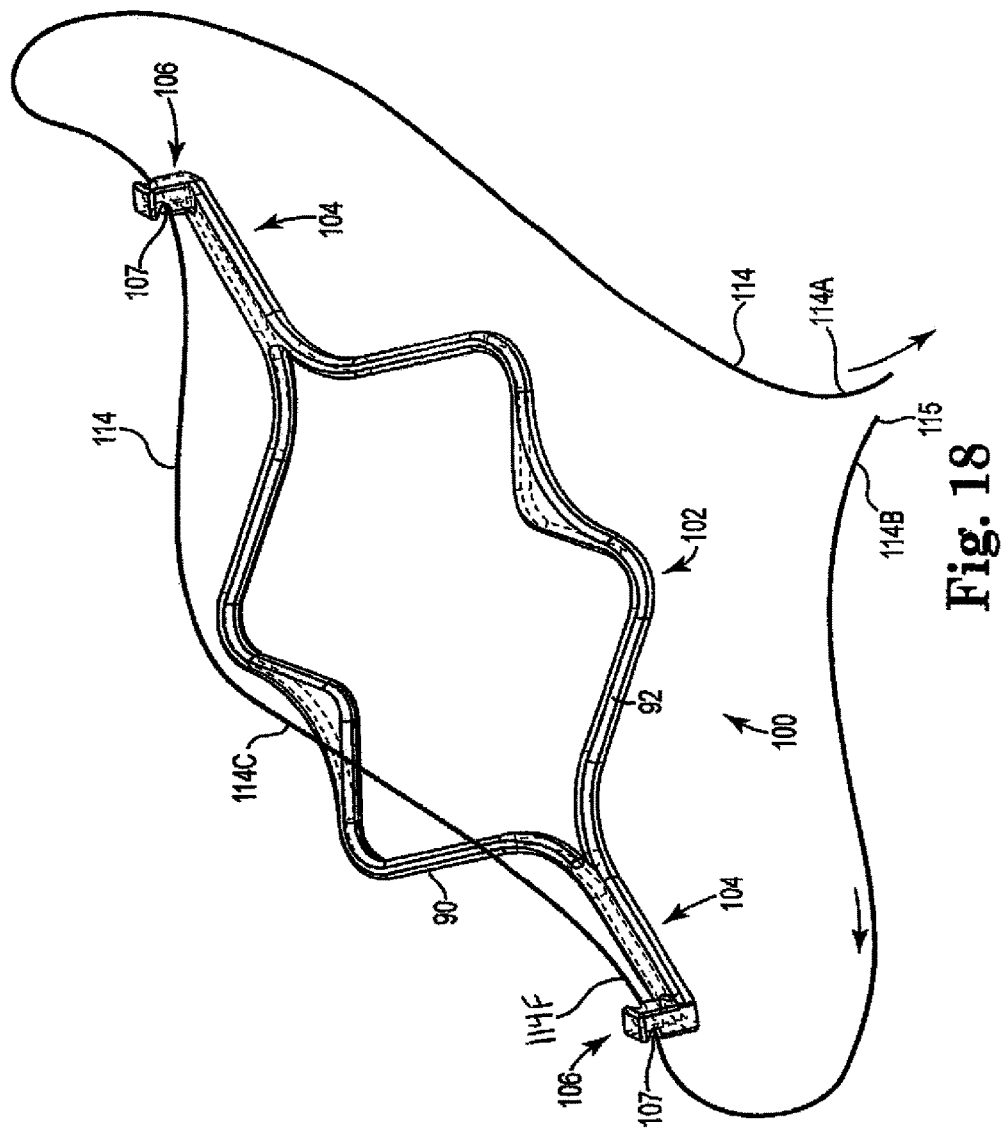

IMPLANTS, TOOLS, AND METHODS FOR TREATMENTS OF PELVIC CONDITIONS

PRIORITY

This application claims the benefit from International No. PCT/US2012/134689, which as granted an International Filing date of Feb. 28, 2012, which in turns claims the priority under 35 U.S.C. § 119(e) from United States Provisional Patent Application having U.S. Ser. No. 61/468,069, filed Mar. 28, 2011, entitled "IMPLANTS, TOOLS, AND METHODS FOR TREATMENTS OF PELVIC CONDITIONS," and U.S. Ser. No. 61/484,062, filed May 9, 2011, entitled "IMPLANTS, TOOLS, AND METHODS FOR TREATMENTS OF PELVIC CONDITIONS," which applications are incorporated herein by reference in their entireties.

FIELD OF THE INVENTION

The present invention relates generally to implants, tools, devices, systems, apparatus, and related methods for treating pelvic conditions including but not limited to incontinence and prolapse conditions in men and women.

BACKGROUND

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

There is a desire to obtain a minimally invasive yet highly effective supportive implant that can be used to treat conditions that include incontinence, pelvic organ prolapse, and others. Moreover, there is ongoing desire to identify methods and implantable supportive implants that are able to be placed efficiently and effectively within a patient in a manner that provides effective or optimal support, and that can be placed with certain efficacy.

SUMMARY

Devices, systems, and methods as described can be applied to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), levator defects, and other conditions caused by muscle and ligament weakness, hysterectomies and the like.

Various surgical tools, implants, procedural improvements are disclosed herein. Certain embodiments of method and implants involve an implant that includes a tension indicator. Optional features include a backer and also a tether that can be attached to the tension indicator, the backer or both, to allow easy removal of the indicator and backer away from the implant.

In one aspect, the invention relates to a surgical implant that includes an implant and a tension indicator. The implant includes a front side and a back side. The implant includes an implantable material having a length that can be increased and decreased. The tension indicator includes: a first fastener secured to a first position of the implant; a second fastener secured to a second position of the implant; a middle segment extending along a length between the first position and the second position; and a cursor located at the middle segment. When length of the implant between the first position and the second position is increased, the cursor moves in a first direction relative to a reference, and when the length of the implant is decreased the cursor moves relative to the reference in a direction opposite the first direction.

In another aspect the invention relates to a surgical implant that includes: an extensible strip, a tension indicator located along a length of the strip, a backer located between the tension indicator and a surface of the extensible strip, and a tether connected to the tension indicator, the backer, or the tension indicator and the backer.

In another aspect, the invention relates to a method of dissembling a surgical implant. The surgical implant includes: an extensible strip, a tension indicator located along a length of the strip, and a releasable fastener that releasably secures the tension indicator to the extensible strip. The releasable fastener includes a tether that connects the tension indicator to the extensible strip. The method includes: pulling the tether to release the tension indicator from the extensible strip, and removing the tension indicator from the extensible strip.

In yet another aspect, the invention relates to a method of assembling a surgical implant having a tension indicator. The method includes: providing an extensible strip having a front side and a back side, and providing a tension indicator. The tension indicator includes: a first post having a first post distal end and first post aperture at the first post distal end, and a second post having a second post distal end and second post aperture at the second post distal. The method includes: placing the tension indicator on the front side of the extensible strip, placing the first post through an aperture of the extensible strip to place the first post aperture at the back side of the implant, placing the second post through an aperture of the extensible strip to place the second post aperture at the back side of the implant, inserting a pin through the first post aperture, and inserting a pin through the second post aperture.

Still another aspect of the invention relates to a method of placing a surgical implant in a patient. The method includes: providing a surgical implant including a tension indicator, placing the surgical implant in a patient while positioning the implant to support tissue, viewing the tension indicator, and adjusting a tension of the implant.

BRIEF DESCRIPTION OF THE DRAWINGS

FIGS. 2, 3, 4, 5, 6, and 7 illustrate embodiments of tension indicators.

FIGS. 13A, 13B, 14A, 14B, 15A, and 15B illustrate embodiments of implants that include a tension indicator, backer, and tether.

FIGS. 16A, 16B, 16C, 17A, 17B, 17C, 17D, 17E, and 17F illustrate embodiments of fasteners.

FIG. 18 illustrates an embodiment of a tension indicator having releasable fasteners.

Figures 1A, 1B:
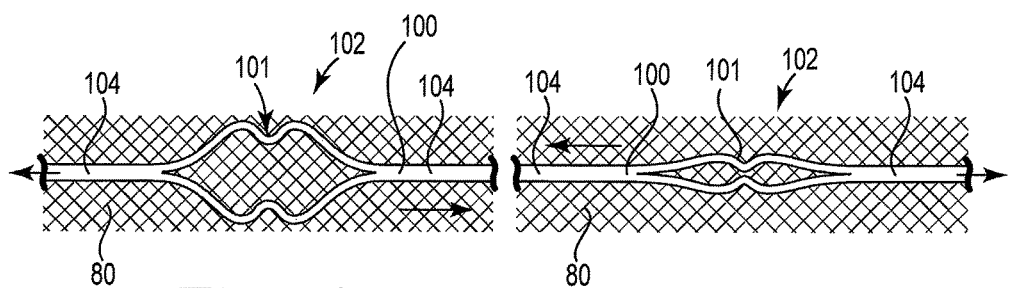
FIG. 1A through 1F illustrate embodiments of tension indicators.
Figures 1C, 1D:
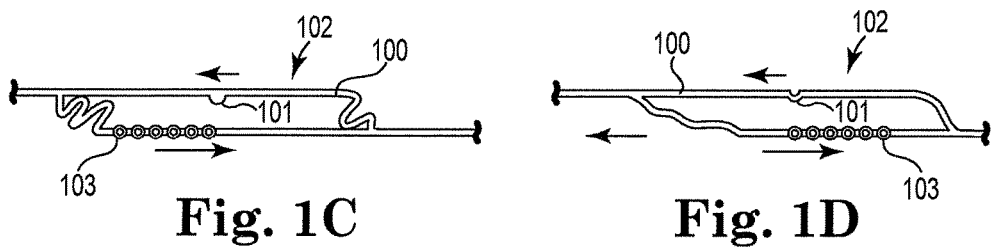

All figures are not to scale.

DETAILED DESCRIPTION

Pelvic floor disorders include urinary and fecal incontinence, prolapse, cystocele, rectocele, enterocele, uterine and vaginal vault prolapse, levator defects, and others, in male and female patients. These disorders typically result from weakness or damage to normal pelvic support systems. Common etiologies include childbearing, removal of the uterus, connective tissue defects, prolonged heavy physical labor and postmenopausal atrophy.

Vaginal vault prolapse is the distension of the vaginal apex, in some cases to an orientation outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons.

Vaginal vault prolapse is often associated with a rectocele, cystocele, or enterocele. It is known to repair vaginal vault prolapse by suturing to the supraspinous ligament or to attach the vaginal vault through mesh or fascia to the sacrum. Many patients suffering from vaginal vault prolapse also require a surgical procedure to correct stress urinary incontinence that is either symptomatic or latent.

Sling procedures for treating urinary incontinence include surgical methods that place a supportive implant such as a sling to stabilize or support the bladder neck or urethra. A variety of different supportive implants and sling procedures are known. Slings and methods can differ based on the type of sling material and anchoring methods used, and placement and technique for placing and supporting the sling, including tissue to be supported. In some cases, a sling is placed under the bladder neck and secured via suspension sutures to a point of attachment (e.g. bone) through an abdominal or vaginal incision. Other techniques place a supportive portion of a sling below a urethra or bladder neck, and support the sling by placement of ends at or through obturator foramen tissue. Examples of sling procedures are disclosed in U.S. Pat. Nos. 5,112,344; 5,611,515; 5,842,478; 5,860,425; 5,899,909; 6,039,686, 6,042,534 and 6,110,101.

As used herein, the term "anchor" refers non-specifically to any structure that can connect an implant to tissue of a pelvic region. The tissue may be bone or a soft tissue such as a muscle, fascia, ligament, tendon, or the like (i.e., supportive tissue). The anchor may be any known or future-developed structure useful to connect an implant to such tissue, including but not limited to a clamp, a suture, a soft tissue anchor such as a self-fixating tip, a bone anchor, and the like.

Systems, devices, tools, implants, etc., described herein are directed to surgical instruments, assemblies, implantable supportive implants, systems, and related methods for treating a pelvic condition including prolapse (e.g., any form of vaginal prolapse), urinary incontinence, fecal incontinence, levator defects, etc., in a male or female patient. An implant can be implanted in a male or a female to treat a condition such as prolapse, urge incontinence, mixed incontinence, overflow incontinence, functional incontinence, and the like.

An implant can include a tissue support portion (or "support portion") that can be used to support a urethra (including a bladder neck), bladder, vagina, levator, rectum, sphincter, or other pelvic tissue. Supporting a "urethra" refers to supporting tissue that includes the urethra (which can refer to the bladder neck), and that can optionally include tissue adjacent to a urethra such as bulbospongiosus muscle, corpus spongiosum, or both. According to specific methods involving treatment of urinary incontinence, a support portion may be placed below bulbospongiosus muscle to support both bulbospongiosus muscle and corpus spongiosum (along with the urethra), or alternately bulbospongiosus muscle may be dissected and a support portion may be placed to contact corpus spongiosum tissue (to support the urethra).

An implant can additionally include one or more extension portion (otherwise known as an "end" portion or "arm") attached or attachable to the tissue support portion. Normally, for treating incontinence, an implant can include two opposing extension portions. Extension portions are elongate pieces of material (e.g., mesh, molded implant material, suture, or biologic material) that extend from the tissue support portion and either are or can be connected to the tissue support portion, and are useful to attach to anatomical features or "supportive tissue" in the pelvic region (e.g., using an anchor such as a self-fixating tip or another form of tissue fastener) to thereby provide support for the tissue support portion and the supported tissue. Generally for treating incontinence, two extension portions can extend from opposite ends of a tissue support portion as elongate "ends," "arms," or "extensions," and may attach to supportive tissue in the pelvic region by extending through a tissue path to an internal anchoring point (see, e.g., Applicant's copending U.S. Patent Application Publication number US 2010/256442, filed Aug. 8, 2008, by Ogdahl, entitled SURGICAL ARTICLES AND METHODS FOR TREATING PELVIC CONDITIONS, the entirety of which is incorporated herein by reference), or may extend to an external incision, such as through an obturator foramen and through an external incision at a groin or inner thigh (see, e.g., Applicant's copending U.S. Patent Publication Number US 2006/0287571, the entirety of which is incorporated herein by reference). Also see U.S. Patent Publication number US 2011/0034759 and WO 2010/093421, PCT/US2010/057879, filed Nov. 23, 2010, and PCT/US2010/059739, filed Dec. 9, 2010, the entireties of which are incorporated hereby by reference.

In exemplary uses, each extension portion can extend from the location of attachment with the tissue support portion, through pelvic tissue, and optionally be attached to supportive tissue within the pelvic region. For certain procedures, the supportive tissue can be tissue adjacent to the urethra such as pelvic fascia; tissue between the urethra and an obturator foramen such as pelvic fascia; or tissue of an obturator foramen such as obturator fascia, obturator internus muscle, obturator membrane, obturator externus muscle, etc. For alternate procedures an extension portion can be sized to extend from the tissue support portion, through an obturator foramen, around a pubic ramus bone, and threaded (subcutaneously) back to a medial location such as near a medial incision. Other locations for different procedures (e.g., prolapse) include a ligament, tendon, or muscle in the pelvic region such as an arcus tendineus, sacrospinous ligament, or levator muscle.

An implant may include portions, pieces, or sections that are synthetic or of biologic material (e.g., porcine, cadaveric, etc.). Extension portions may be, e.g., a synthetic mesh such as a polypropylene mesh, a suture, a biodegradable suture, a molded implant material, or the like. The tissue support portion may be synthetic (e.g., a polypropylene mesh or a molded material) or biologic. Examples of implant products that may be similar to those useful according to the present description include those sold commercially by American Medical Systems, Inc., of Minnetonka Minn., under the trade names Apogee®, Perigee®, and Elevate® for use in treating pelvic prolapse (including vaginal vault prolapse, cystocele, enterocele, etc.), and Sparc®, Bioarc®, Monarc®, MiniArc®, InVance™, and Advance™ for treating urinary incontinence.

An example of a particular type of pelvic implant is the type that includes supportive portions including or consisting of a tissue support portion and two or four extension portions extending from the tissue support portion. An implant that has exactly two or four extension portions can be of the type useful for treating urinary incontinence or vaginal prolapse. The term "supportive portions" refers to portions of an implant that function to support tissue after the implant has been implanted and specifically includes extension portions and tissue support portions, and does not include optional or appurtenant features of an implant such as a sheath, tensioning suture, tissue fastener, or self-fixating tip or other type of connector for attaching the implant to an insertion tool.

Dimensions of a tissue support portion can be any dimensions useful to support a specific tissue, e.g., urethral or vaginal tissue, for treating a pelvic condition such as incontinence, prolapse, or another pelvic condition. A tissue support portion for use in treating incontinence can be of sufficient length to support and optionally partially surround a urethra or urethra-supporting tissue. A width of a tissue support portion may optionally and preferably be greater than a width of extension portions and can be sufficiently wide to increase contact area and frictional forces between a tissue support portion and a tissue in contact with the tissue support portion. Exemplary lengths of a tissue support portion can be in the range from 0.5 to 2 inches, such as from 0.75 to 1.5 inches. Exemplary widths of a tissue support portion can be in the range from 0.4 or 0.5 to 4 centimeters, such as from 1 to 2.5 or 3 centimeters. (A tissue support portion may be part of a support portion piece that includes the tissue support portion and optionally some amount of opposing extension portions extending from ends of the tissue support portion.)

An implant (e.g., sling) for placement against a corpus spongiosum for treatment of urinary incontinence in a male patient may optionally and preferably include a widened central support to provide increased contact and frictional engagement with the corpus spongiosum. See, for example, Assignee's copending U.S. Patent Publication Number US 2006/0287571 and U.S. Pat. No. 7,422,557, the entireties of these applications being incorporated herein by reference.

Dimensions of extension portions can allow the extension portion to reach between a tissue support portion placed to support a pelvic tissue such as tissue of a urethra, vagina, anal sphincter, levator, etc. (at an end of the extension portion connected to the tissue support portion) and a location at which the distal end of the extension portion attaches to supportive tissue at or about the pelvic region. Exemplary lengths of an extension portion for use in treating incontinence, for example, measured between a connection or boundary between the extension portion and the tissue support portion, and a distal end of the extension portion, can be, e.g., from 0.5 to 2.75 inches, preferably from 1.0 to 2.25 inches, and the length can optionally adjustable. These or other lengths will be useful for implants designed to treat other conditions. As described elsewhere herein, a length of an extension portion may be fixed (i.e., the extension portion does not include any form of length-adjustment mechanism). Alternate embodiments of implants may include an adjusting engagement that allows a physician to alter the length of an extension portion before, during, or after implantation.

Implants as described can include a tissue fastener at a distal end or a distal portion of an extension portion, which is the end or portion not attached to a tissue support portion. (The term "distal" as used in this context generally refers to location at an end of an extension portion away from a tissue support portion.) A tissue fastener at a distal end or portion of an extension portion can be any of various types, including: a self-fixating tip that is inserted into soft tissue and frictionally retained; soft tissue anchors; biologic adhesive; a soft tissue clamp that can generally include opposing, optionally biased, jaws that close to grab tissue; and opposing male and female connector elements that engage to secure an end of an extension portion to tissue. (See International Patent Application No. PCT/US2007/014120, entitled "Surgical Implants, Tools, and Methods for Treating Pelvic Conditions, filed Jun. 15, 2007; U.S. patent application Ser. No. 12/223,846, filed Aug. 8, 2008, entitled SURGICAL ARTICLES AND METHODS FOR TREATING PELVIC CONDITIONS; U.S. patent application Ser. No. 12/669,099, filed Jan. 14, 2010, entitled PELVIC FLOOR TREATMENTS AND RELATED TOOLS AND IMPLANTS; and WO 2009/075800, the entireties of which are incorporated herein by reference.) An implant may also have one or more extension portion that does not include a tissue fastener, for example if the distal end is designed to be secured to tissue by other methods (e.g., suturing), or is intended to pass through an obturator foramen and a tissue path around a pubic ramus bone, in which case the extension portion may optionally include a connector, dilator, or dilating connector, which connects to an elongate tool that can be used to either push or pull the connector, dilator, or dilating connector through a tissue path (e.g., to a medial incision).

One embodiment of a tissue fastener is a self-fixating tip. A "self-fixating tip" in general can be a structure (sometimes referred to as a soft tissue anchor) connected at a distal end of an extension portion (or extension portion piece) that can be implanted into soft tissue (e.g., muscle, fascia, ligament, etc.) in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through and into tissue for implantation, preferably also through an incision to reach the interior of the pelvic region, e.g., at a location of an obturator foramen or other supportive tissue. The insertion tool may engage the self-fixating tip at an internal channel of the self-fixating tip, at an external location such as at an external surface of the base, at a lateral extension, or otherwise as desired, optionally in a manner to allow the insertion tool to push the self-fixating tip through an incision in a patient and through and into supportive tissue.

Exemplary self-fixating tips can include one or more lateral extensions that allow the self-fixating tip to be inserted into soft tissue and to become effectively anchored in the tissue. A lateral extension may be moveable or fixed. The size of the self-fixating tip and optional lateral extensions can be useful to penetrate and become anchored into the tissue. Exemplary self-fixating tips are described in Assignee's copending international patent application PCTUS2007/004015, filed Feb. 16, 2007, titled Surgical Articles and Methods for Treating Pelvic Conditions, the entirety of which is incorporated herein by reference. Other structures may also be useful.

According to exemplary embodiments, a self-fixating tip can have structure that includes a base having a proximal base end and a distal base end. The proximal base end can be connected (directly or indirectly, such as by a connective suture) to a distal end of an extension portion. The base extends from the proximal base end to the distal base end and can optionally include an internal channel extending from the proximal base end at least partially along a length of the base toward the distal base end. The optional internal channel can be designed to interact with (i.e., engage, optionally by means of a release mechanism that can be selectively engaged and released) a distal end of an insertion tool to allow the insertion tool to be used to place the self-fixating tip at a location within pelvic tissue of the patient. A self-fixating tip can be made out of any useful material, generally including materials that can be molded or formed to a desired structure and connected to or attached to a distal end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

According to various systems as described, one or more instrument, insertion tool, adjusting tool, or the like, may be incorporated or used with an implant or method as described. Examples of useful tools include those that generally include one or more (stationary or moveable) thin elongate, relatively rigid shaft or needle that extends from a handle. The shaft can be a single elongate shaft or multiple separate elongate shafts extending from the handle, or one or more primary shaft that extends from the handle and that contains multiple branch or "tine" shafts that separate at the end of the primary shaft. The handle is located at a proximal end of the device and attaches to one end (a proximal end) of a shaft. According to some embodiments, a distal end of one or more shaft can be adapted to engage a portion of an implant such as a tissue fastener (e.g., a self-fixating tip), in a manner that allows the insertion tool to engage and push the tissue fastener through a tissue passage and connect the tissue fastener to supportive tissue of the pelvic region. Examples of this type of tool can be used with a self-fixating tip that includes an internal channel designed to be engaged by a distal end of an insertion tool to allow the self-fixating tip to be pushed into tissue. Other general types of insertion tools will also be useful, but may engage a self-fixating tip or other tissue fastener in an alternate manner, e.g., that does not involve an internal channel.

Exemplary insertion tools for treatment of incontinence and vaginal prolapse are described, e.g., in U.S. Pat. Nos. 7,500,945; 7,070,556; 7,422,557; 7,740,576; 7,351,197; 8,535,217; and 9,226,809; and US Patent Publication No. 2010-0256442 the entireties of these documents being incorporated herein by reference.

A tool according to the invention can optionally include a mechanism (a "release mechanism") by which a tissue fastener (e.g., a self-fixating tip) can be securely and releasably engaged with a distal end of an insertion tool such that the tissue fastener can be selectively secured to the distal end mechanically, then selectively released. With a releasable engagement, a tissue fastener (e.g., self-fixating tip) can be released from the distal end by releasing the engagement (e.g., mechanical engagement) by movement of an actuator at the proximal end of the insertion tool, such as at the handle. For example, an internal channel (or external surface) of a self-fixating tip can include an engaging surface designed to engage a mechanism at a distal end of an insertion tool while the self-fixating tip is placed at, on, or over the distal end. As an example, an internal or external surface of a self-fixating tip can include a depression, ring, edge, or ledge, that can be rounded, angular, etc. A mechanical detent such as a pin, ball, spring, deflector, or other surface or extension located at the distal end of the insertion tool can be moved, deflected, or extended relative to the distal end of the insertion tool to contact the surface of the self-fixating tip to securely and releasably hold the self-fixating tip at the distal end of the insertion tool and prevent removal of the tip from the distal end until removal is desired. The detent (or other surface or mechanism) can be cause to extend (or retract) from the distal end of the insertion tool by actuating a trigger or other mechanism located at the proximal end (e.g., handle or a proximal location of a shaft) of the insertion tool, to secure (or release) the self-fixating tip. Upon placement of the self-fixating tip at a desired location during a surgical implantation procedure, the insertion tool operator can release the self-fixating tip by use of the trigger or other mechanism at the handle to disengage the detent and cause the tip to become loose. The insertion tool can then be removed from the tissue path and the self-fixating tip can remain in a desired implanted location.

According to various embodiments of implants described herein, an implant can include multiple pieces that are adjustably connected together by an adjusting engagement. A "multi-piece" implant refers to an implant that includes a "support portion piece" and one or multiple "extension portion piece" as separate pieces of the implant. An extension portion piece can be separate from a support portion piece, and the two pieces can be connected through an adjustable engagement. The support portion piece includes a tissue support portion.

An adjusting engagement may be for example a one-way adjusting engagement, a two-way adjusting engagement, or a locking two-way engagement, that allows a portion, piece, or a segment of an implant to be moved relative to another portion, piece, or segment if the implant and adjusted as to length, tension, or positioning. Examples of adjusting engagements are described, for example, in Examples of adjusting engagements are described, for example, in Applicant's copending U.S. Pat. No. 8,834,350, entitled SURGICAL IMPLANTS AND TOOLS FOR TREATING PELVIC CONDITIONS, and U.S. Pat. No. 8,597,173; entitled PELVIC FLOOR TREATMENTS AND RELATED TOOLS AND IMPLANTS, the entireties of which are incorporated by reference.

Some adjusting engagements can allow two-way movement of one piece relative to another piece (e.g., a "two-way" adjusting engagement). This type of adjusting engagement allows movement of a segment of implant (e.g., of a segment or portion of an extension portion piece) in two directions through an adjusting engagement. The force needed to move the segment of implant in one direction is substantially equal to the force needed to move the segment in the opposite direction, and, optionally, the two-way adjusting engagement does not substantially hinder the movement of a segment of implant through the adjusting engagement with frictional surfaces such as extensions (e.g., "teeth") extending into an aperture through which the segment of implant is moved. As an example, a two-way adjusting engagement may include an open (smooth) aperture that may be circular, oval, square, elongate, or rectangular, such as in the form of a circle, slit, or slot, etc. The aperture may optionally be reinforced by a reinforced perimeter of a shape that is similar to the aperture, such as by a fabric or a polymeric material such as a grommet (e.g., a "loose grommet" or "eyelet"), which may be circular, square, rectangular, or of any desired shape. The reinforced perimeter (e.g., grommet) defines a reinforced aperture through which a segment of implant can pass relatively freely and with the same resistance two different directions.

A two-way adjusting engagement may optionally be capable of an open and a closed (e.g., locked) configuration, the open configuration allowing two-way movement between the pieces, and the closed (or locked) configuration preventing any movement between the pieces. Such an adjusting engagement may be referred to as a locking two-way adjusting engagement, and may include any form of mechanical securement device that can be configured in an open configuration (to allow two-way movement between pieces) and a closed configuration (to prevent movement between pieces). The locking two-way adjusting engagement may be selectively and reversibly moveable between the open configuration and the closed configuration, or may instead initially be an open configuration that, once placed in a closed configuration, cannot be re-configured to the open configuration. Examples of structures that may be part of a locking two-way adjusting engagement include a mechanical clip, staple, stitch, detent, or rivet; any form of spring-loaded or moveable frictional engagement; a non-moveable frictional engagement such as a slot, slit, cleat, or other non-moveable aperture or opening through which a portion of implant can be selectively engaged, released, and re-engaged; a deformable opening, ring, clip, staple, etc., which may be generally open and then permanently closed by mechanical deformation; and the like. One form of exemplary structure may be forcibly closed (e.g. by bending a part until permanent deformation or closing a part until some latch or similar feature snaps shut), while others may be biased to close (e.g. a spring-loaded clip is held open until released so it can clamp shut). Changing from an open to a closed orientation could be performed by an independent tool, or may be an additional feature built into the adjustment tool. The clip or alternate opening-closing structure could be attached to larger structure of an adjusting engagement (potentially integrated into its design), or separate (so it could be loaded into the tool).

Other adjusting engagements may allow for one-way adjustment such as shortening of a length of an extension portion. These adjusting engagements can be referred to as "one-way" adjusting engagements, and allow adjustment of a length of an implant portion (e.g., extension portion) in one direction and not (or not easily) in an opposite direction. An exemplary one-way adjusting engagement can include an aperture through which a segment of implant (e.g., a portion of an extension portion piece) can extend, and one or multiple surfaces (e.g., extensions or teeth) that frictionally engage the segment of implant passing therethrough, e.g., by extending into or toward the aperture or otherwise contacting the segment of implant to inhibit movement of the segment of implant relative to the adjusting engagement. The one-way engagement can preferentially allow movement of the segment of implant through the aperture in one direction while inhibiting or preventing movement of the segment of implant in an opposing direction.

One form of implant useful for treatment of urinary incontinence is a "mini-sling," or "single incision sling,"

(e.g., as marketed by American Medical Systems under the trade name MINIARC™), which is a faster and less invasive procedure for treating stress urinary incontinence. Designs described herein are also useful for female pelvic floor repair products, male incontinence, for treating prolapse (e.g., vaginal prolapse), levator defects, anal incontinence, and other pelvic conditions.

A feature of an implant as generally described herein is a tension feedback indicator (or, herein, "tension indicator" or "indicator"). A tension feedback indicator is a device associated with an implant that allows for a user (e.g., surgeon or doctor) to identify a level of tension applied to an implant or portion of an implant such as an extension portion or a tissue support portion, during a surgical procedure in which the implant is placed in a patient. Certain tension feedback indicators as described herein can allow for simple visual indication of tension applied to an implant segment (e.g., a mesh, biologic, or a molded material) during a surgical procedure. Any of the tension feedback indicators described can be used with any implant that, during installation, includes a tension or length that is desirably measured, gauged, or quantitatively or qualitatively assessed; these include any of the implants generically or specifically described herein that either include or do not include an adjustment mechanism (e.g., an adjusting engagement or other form of adjustment mechanism), any implant previously or presently known to be useful for treating a pelvic condition, and implants developed in the future for treating a pelvic condition.

A tension indicator can allow for simple and easy measurement and indication of an amount of tension placed on a length of implant or a piece or portion of an implant (e.g., an extension portion or a tissue support portion) during surgical placement of the implant in a patient. No additional tool or instrument is needed, as feedback is provided by the tension indicator attached to the sling itself. The feedback is provided as the implant is being placed, so there is no need to pause during placement to check tension then re-engage and finish placement. A surgeon is able to apply consistent tension during placement of an implant. The tension indicator can be attached to any type of implant provided that the implant material has consistent elongation through the measured segment being tensioned.

The tension feedback indicator can be a device placed onto a portion of an implant, such as a length of an elongate portion of an implant, that will be affected based on the degree of tensioning of the implant. Generally a length of implant will stretch or lengthen when tension is placed on the length of implant. A tension feedback indicator, fixed at two locations along the length of implant, can change form based on the changing or changed length of the implant. As an example, a tension feedback indicator may change shape, such as a length or height, upon tensioning of an implant portion to which the tension feedback indicator is attached. The degree or extent of the change in shape (e.g., length) can be correlated to an amount of tension that is being placed along the length of implant.

These and other types of tension feedback indicators can include an overall structure that includes a central, deformable or flexible middle segment located along a length of the indicator, between two ends that attach to an implant. The middle segment can be extensible, e.g., can include one or more spring segment that allows extension when the tension indicator is pulled length-wise, such that tension is applied by pulling the ends in opposite directions. The middle segment also returns substantially to an original size, shape, and form when allowed to, such as when the tension is removed. When the ends are attached to an implant and the implant is lengthened, the deformable middle segment is deformed in a manner that allows the middle segment to become lengthened, and the attached ends remain attached to the lengthening implant. The flexible middle segment allows the indicator to lengthen upon lengthening of the implant to which the tension feedback indicator is attached, and can preferably return to a non-lengthened form when tension in the implant is released.

According to other optional features that can be included with a tension feedback indicator, a combination of a cursor and a reference can allow for quick and easy assessment of a desired level of tension applied to an implant during a surgical procedure. A cursor can be a structure on a middle segment of a tension indicator that can be identified visually. Specific examples of structures that may act as a cursor include a single structural feature or a set of features located at a middle segment of a tension indicator, such as a boundary, line, marking (e.g. printed or structural marking), arrow, point, angle, needle, bulb, ball, opening, etc., or a series or combination of these. Optionally and preferably, to provide for improved potential for visualizing a cursor and a reference, a cursor and a reference can be located at a location of an implant that can be visible through a surgical incision; for treating incontinence, a cursor and reference can optionally be located at a midpoint or midline of a length of an implant, e.g., at a location that will be at or near the urethra when the implant is being placed therapeutically.

A reference can be a physical structure or marking (indicia) (one or multiple) present on a tension indicator, a backer (see below), or at another location of the implant. An amount of tension placed on the implant at a location of the tension feedback indicator can be correlated to a change in length (i.e., the elongation) of the implant segment, which can in turn be indicated by the tension indicator by a comparison of the location of the cursor to one or more physical reference (e.g., demarcation, structure, indicia, or the like) located on the implant, on the tension feedback indicator, on a backer, or on a combination of these.

The reference may include one or a series of demarcations relative to which a cursor will move upon lengthening of the tension indicator. A reference may generally be any marking, such as coloration or one or multiple molded or cut physical structures of an implant, implant piece or portion (e.g., mesh), tension indicator, or backer. Specific examples of structures that may act as a reference include a single structural feature or a set of features of a backer, such as an aperture, a boundary, curved or straight line, marking, arrow, point, angle, needle, bulb, ball, opening, etc., or a series or combination of these. An alternate form of a reference can be a printed reference located on a backer, a portion of an implant, or the tension indicator. A printed reference may be a single marking or a series of marks that allows the relative location of a cursor of the tension indicator to be visually compared to the reference.

Each end of a tension indicator can be attached to the implant by a fastener. The fastener can be a "releasable fastener" that allows the tension indicator to be released from the implant and removed from the implant and the patient after use during a surgical procedure. A "releasable fastener" is a fastener that can be operated on manually (including by use of a surgical tool such as a scissors) (after the implant has been implanted in a patient) to release the fastener and the tension indicator from the implant and allow the tension indicator to be removed from the patient. The implant remains in the patient and will function to support tissue after the tension indicator is removed.

One example of a releasable fastener can include a post at an end of a tension indicator. A post can connect to the tension indicator at one end of the post, e.g., a "base," and can extend along a length to a distal post end. The post can be attached to an implant material by extending from an end of a tension indicator located on one side of an implant, through the implant (e.g., through an aperture or hole in the implant) and to a second side of the implant (the distal end of the post becomes located on the second side of the implant). The distal end of the post can include a rivet-type expanded head that releasably secures the post in position through the implant. The expanded rivet head can be pushed through a compliant aperture of the implant (mesh) to place the post for using the tension indicator during a surgical procedure. During use the post is held in the implant aperture by the size of the expanded head. At a time after use, the post can be removed by manually pushing, pulling, or otherwise moving the expanded rivet head back through the compliant aperture of the implant.

Another example of a releasable fastener can include a post at an end of a tension indicator that extends from the end of the tension indicator located on one side of an implant, through the implant (e.g., through an aperture or hole in the implant) and to a second side of the implant, the post being held in place by a pin (e.g., a suture or tether) placed through a hole or aperture located at a distal end of the post and also on the second side of the implant. According to a specific example, this releasable fastener type can be a post-suture engagement wherein the pin can be in the form of a tether (e.g., a suture) passing through an aperture or hole at a distal end of the post. Even more preferably, the tension indicator can include two separate releasable fasteners, each including a post and each post having an aperture at its distal end. The aperture may be in any orientation, e.g., in a direction aligned with a length of the implant, in a direction aligned with at width of the implant, or a at any angle therebetween. A single tether can be passed through both apertures of the posts. The two posts (secured to the implant by the single tether) can hold the tension indicator in place on one side of the implant during a surgical procedure.

After placement of the implant, the tether (e.g., suture) can be pulled away from the posts, removing the tether from the apertures in the posts. As explained elsewhere, a first segment of the tether that engages a post or two posts can preferably disengage the post or posts before a different (second) segment of the tether (that connects to the tension indicator, backer, or both) begins to pull the tension indicator, backer, or both, away from the implant. With the first segment of the tether disengaged from and removed from the apertures of the posts, the tension indicator is no longer engaged to the implant. The tether can be pulled farther away from the implant to remove slack from the (second) segment engaged to the two posts, causing the attached end of the tether to engage and place pressure in the tension indicator, the backer, or both, and be pulled still farther away from the implant to remove the tension indicator, backer, or both from the implant and from the patient.

A tether attached to the tension indicator, a backer, or both, can be an optional feature of a tension indicator, or an implant or system that includes a tension indicator. The tether can allow the tension indicator, backer, or both, to be removed from an implant and a patient at a desired time, by pulling the tether away from the implant and out of the patient. A tether can be in the form of an elongate tape, suture, wire, filament (e.g., monofilament), cord, or other elongate structure that can be attached to a tension indicator, a backer, or both, and grasped and manipulated to move and carry the tension indicator, backer, or both, away from an implant and out of or away from a patient.

In certain preferred embodiments a tether can include a length that has two ends and multiple segments. One segment (e.g., near one tether end) can be securely attached to a tension indicator, a backer, or both, on one side of an implant, to allow the tether to carry the tension indicator, a backer, or both, away from the implant and a patient. Another (e.g., second) segment (e.g., near a second tether end) can be removably attached to a structure (e.g., a post or multiple posts) of a tension indicator extending through the implant to a second side of the implant. The second segment can be disengaged from the pin (or pins) by pulling the tether away from the implant to release the second segment from the pin (or pins), and to thereby release the tension indicator from the implant. The tether can be pulled farther away from implant, removing the tension indicator and optional backer attached to the first segment.

According to these embodiments, an operable length of the second segment can preferably be shorter than an operable length of the first segment. Also optionally a knot, tab, or a knot and a tab, can be located along the length of the tether at the location that defines an end of the first segment. For example, a first segment can be defined as a length of the tether between a tab or adjacent knot, and an end of the tether that connects to the indicator, backer, or both. A second segment can be defined as a length of the same tether that extends from the opposite end, which is generally a loose end, to a location at which the tether engages a post or other fastener (removable fastener); if the indicator has two posts and the tether extends through an aperture of each post, the length of the second segment can be the length from the loose end to the post that the tether disengages from second (or last) when the tether is being pulled away from the implant. This length of the second segment can preferably be shorter than the length of the first segment. According to certain methods, after placing the implant as desired, viewing the tension indicator and optionally adjusting tension in the implant, a user can pull the tether by grasping (manually or with a surgical tool such as a forceps) a knot, tab, or location along the length of the tether and pulling away from the implant. The second segment of the tether, which that engages the two posts, can preferably be pulled to disengage the posts, while slack remains in the fist segment. After the second segment has been completely disengaged from the connective engagement with the posts, the slack in the first segment of the tether (which connects to the tension indicator, backer, or both) is removed by pulling the tab or knot farther from the implant. After the slack in the first segment is removed the tether begins to pull the tension indicator, backer, or both, away from the implant to remove the tension indicator, backer, or both from the implant and from the patient.

According to various embodiments, a tether passing through the aperture in the posts can be a closed loop or an open unlooped segment of the tether. If a closed loop, the tether can be cut at one location to release the tether from the two posts. A loop or at least some portion of the tether or an attachment (e.g., tab) of the tether can preferably be large or long enough to be accessible by extending beyond the dimensions of the implant to allow the loop, tab, or tether to be accessed after placement of the implant in a patient, and then optionally be cut using a surgical instrument, then removed to allow removal of the tension indicator and optional backer.

Figures 1E, 1F:
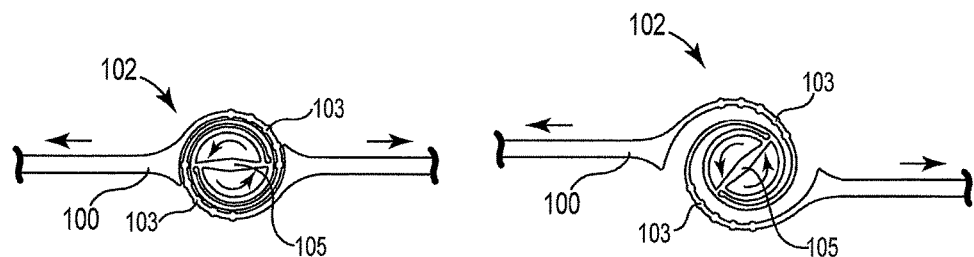

FIGS. 1A through 1F illustrate various embodiments of tension feedback indicators 100 that include a flexible middle segment 102; optional structure that can function as a cursor or reference (colored, structural, or both) 101, 103, and 105; two arms or ends 104 for securing to an implant; and optional fasteners (posts) 106 (not shown) that can be inserted into an aperture of an implant such as a mesh (80). Three exemplary designs include those designated as an "aperture" design (FIGS. 1A and 1B), a "parallelogram" design (FIGS. 1C and 1D), and a spiral or circular "spring" design (FIGS. 1E and 1F). Each of these embodiments is shown in an unextended state (1A, 1C, and 1E) and an extended state (1B, 1D, and 1F) in which opposing ends are pulled in opposite directions along the length of the tension indicator and mesh. The extended state occurs when ends 104 are pulled away from each other in the directions of the arrows, such as when ends 104 are fastened to an extended mesh.

FIGS. 2, 3, 4, 5, 6, and 7 illustrate tension indicators 100 that include physical features that can function as a cursor or as a reference (101, 101A, 103, 105, and others, any of which may be colored or non-colored relative to the balance of the indicator (or an attached implant or an optional backer), and that are molded or cut into a flexible middle segment (102) to indicate a degree of lengthening of the indicator.

Referring to FIG. 2, two opposing cursors (corners, points, or arrows) 101 at a mid-portion of middle segment 102 will move relative to each other (i.e., away from each other) as ends (or "arms") 104 are moved away from each other (see directional arrows near ends 104). Two other opposing cursors (corners, points, or arrows) 101A, also located at a mid-portion of middle segment 102, will move relative to each other (i.e., toward each other) as arms 104 are moved away from each other. Middle segment 102 includes upper connector 90 and lower connector 92 extending between opposite arms 104. Opposing cursors 101 will also move relative to cursors 101A, as ends 104 are moved away from each other.

Figure 3:
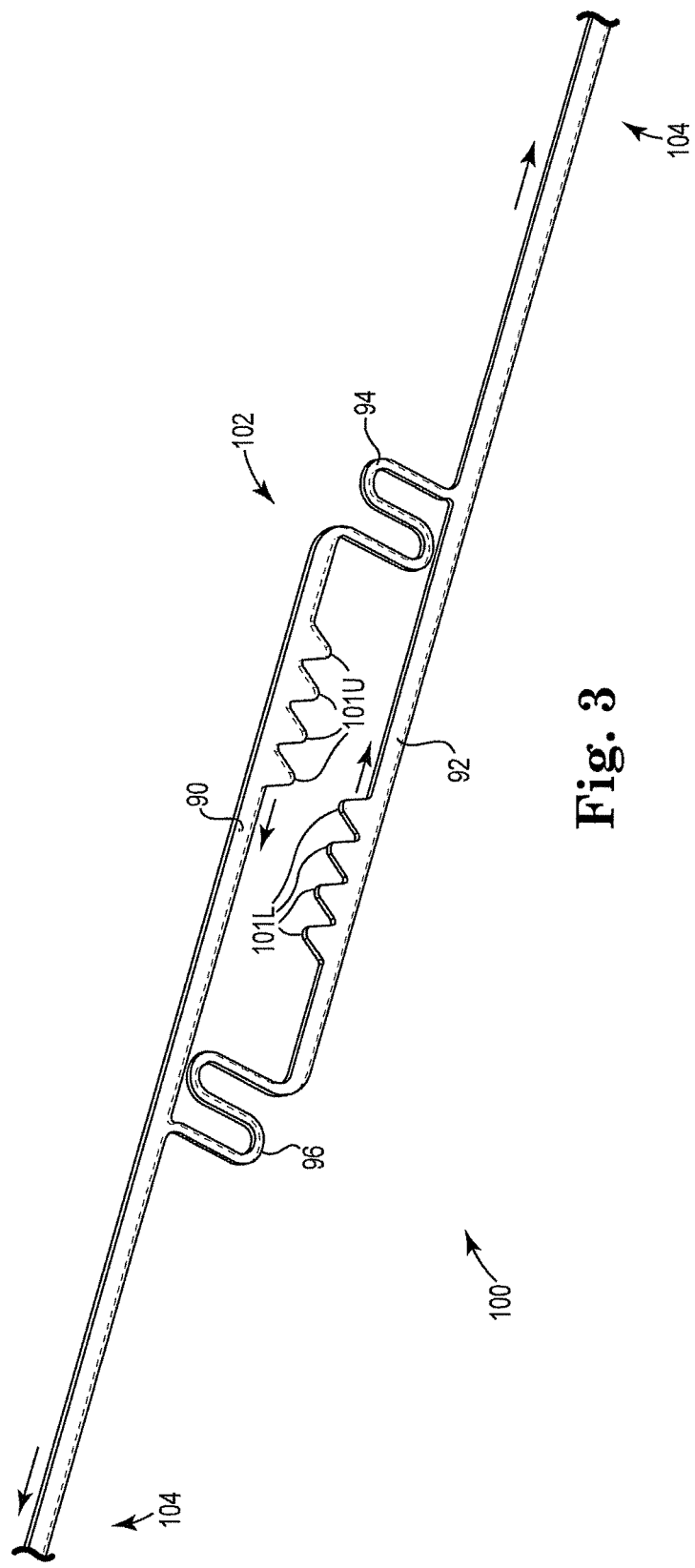

Referring to FIG. 3, indicator 100 includes two opposite ends 104 connected by upper connector 90 and lower connector 92. Each of upper connector 90 and lower connector 92 includes a set of cursors (arrows, bends, kinks, or corners, 101U 101L), and a set of spring segments 94 and 96. In use, cursors 101U at a mid-portion of flexible middle segment 102 will move laterally relative to a second set of arrows 101L as ends 104 are moved away from each other (see directional arrows near ends 104).

Figure 4:
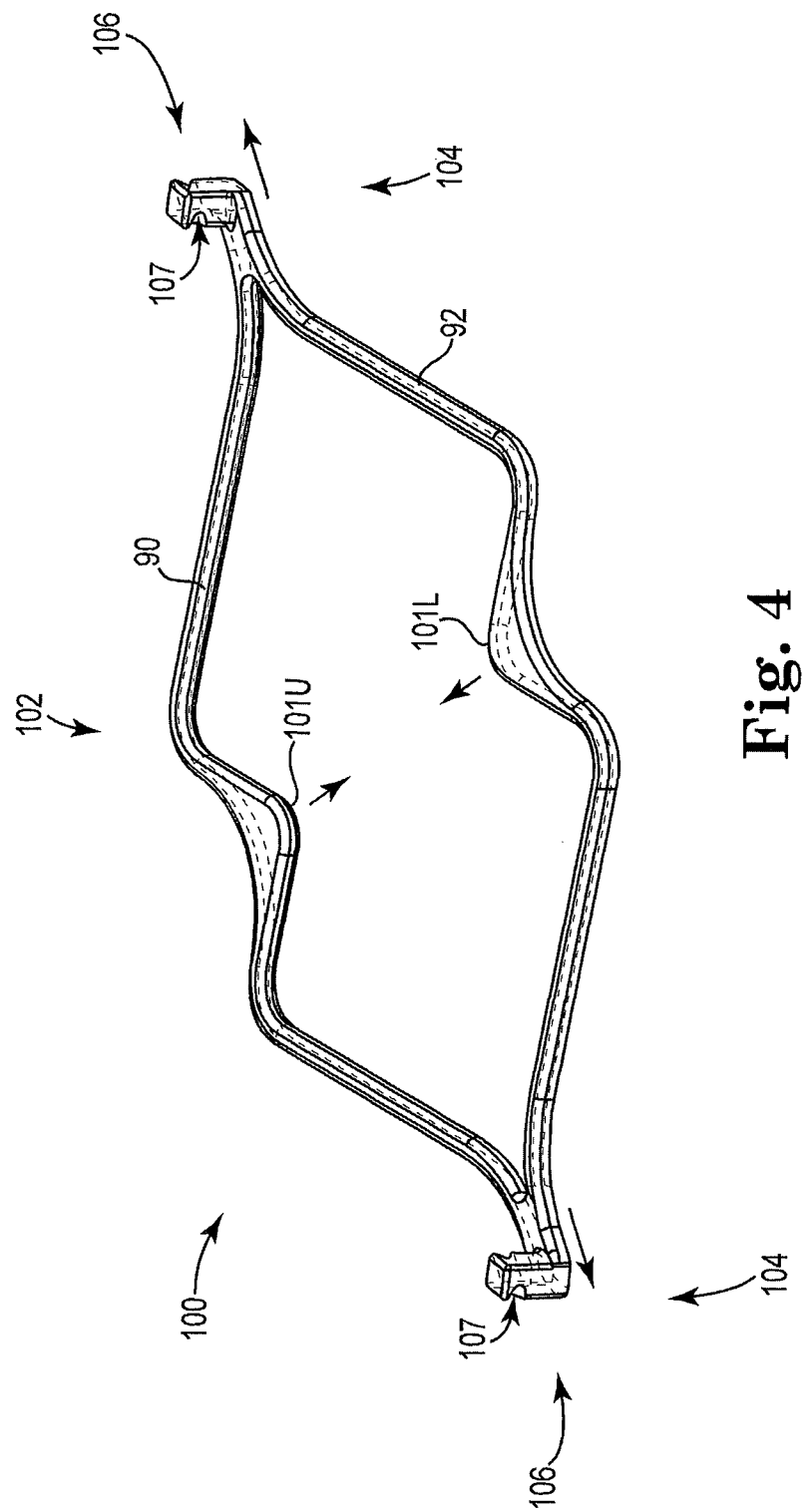

Referring to FIG. 4, indicator 100 includes two opposite ends 104, posts 106 with apertures 107 at distal post ends, and upper connector 90 and lower connector 92. Each of upper connector 90 and lower connector 92 includes a cursor (arrows, bends, kinks, or corners 101U and 101L), which may optionally be colored. In use, cursors 101U and 101U will move toward each other as end segments 104 are moved away from each other (see directional arrows near ends 104). As illustrated, apertures 107 are oriented to become aligned with a length of an implant when posts 106 are inserted through an aperture of an implant. Alternately, apertures 107 can be directed in any other orientation, e.g., at an angle 90 degrees to the apertures as illustrated to align the apertures with a width of the implant.

Figure 5:
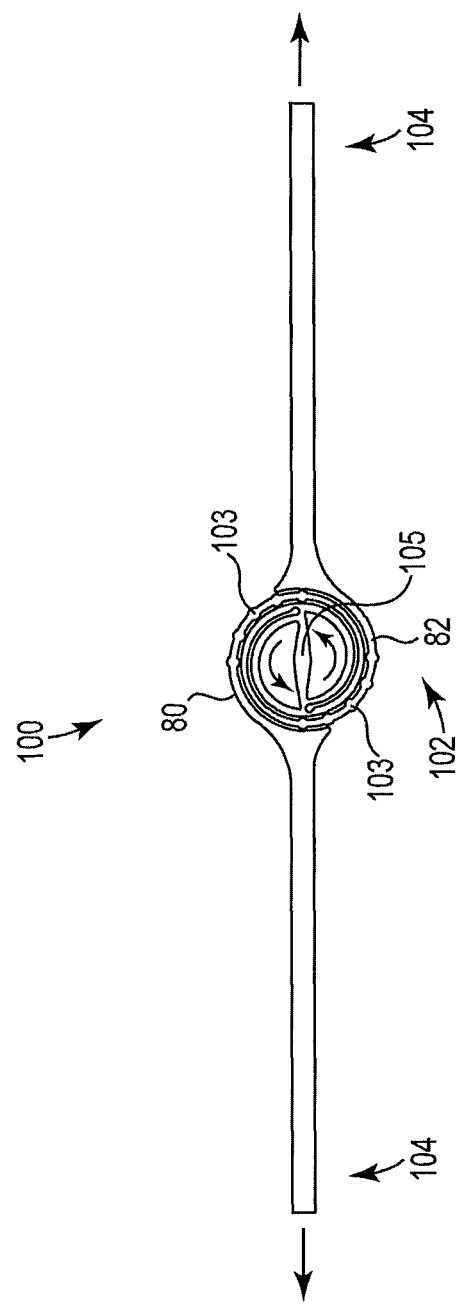

Referring to FIG. 5, indicator 100 includes two opposite ends 104 and opposing spring or coil segments 80 and 82, each comprising a spiral or circular spring or coil. One end of each spiral spring segment 80 and 82 is connected to an end 104, and the other end of each spiral spring segment 80 and 82 is connected to central bar 105. Cursors (circles or beads) 103 at each of spiral spring segments 80 and 82 will move relative to cursor (or reference) (bar) 105, which will turn counter-clockwise as ends 104 are moved away from each other (see directional arrows near ends 104).

Figure 6:
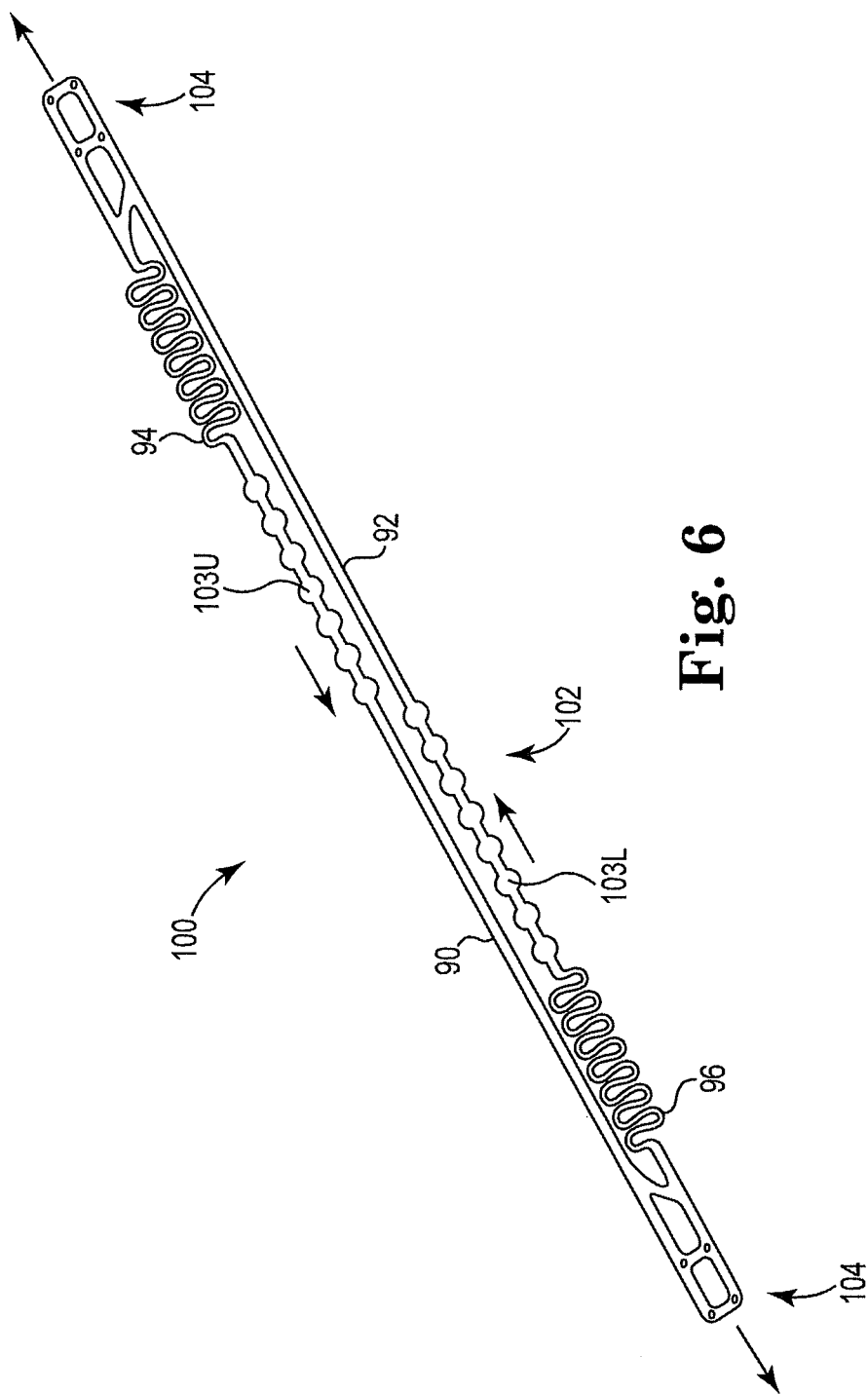

Referring to FIG. 6, indicator 100 includes two opposite ends 104, upper connector 90, and lower connector 92. Connectors 90 and 92 include spring segments 94 and 96, and cursors (circles or beads) 103U and 103L. Cursors 103U will move relative to cursors 103L, as end segments 104 are moved away from each other (see directional arrows near ends 104).

Figure 7:
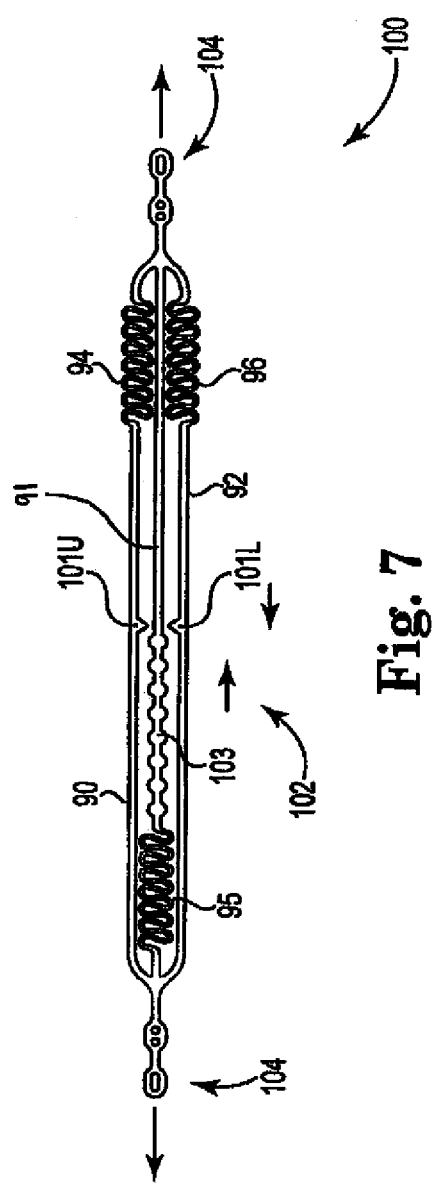
Figure 8:
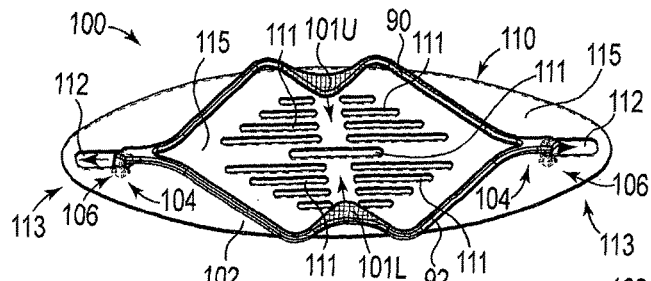
FIGS. 8 through 12 illustrate embodiments of tension indicators and backers.
Figure 9:
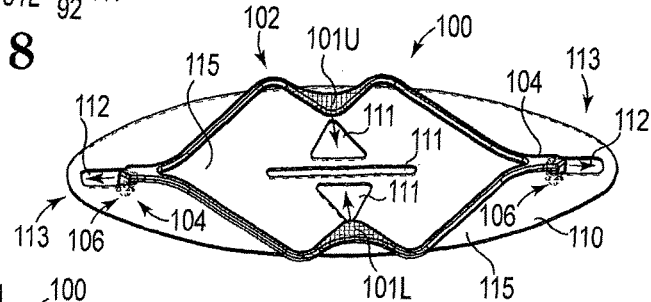
Figure 10:
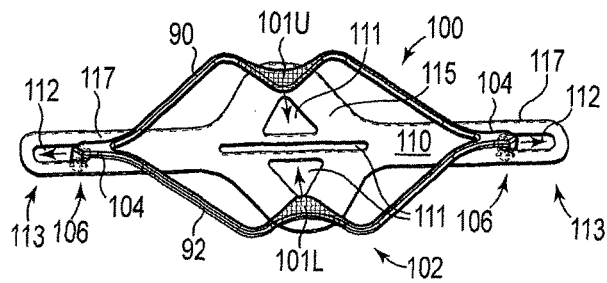
Figure 11:
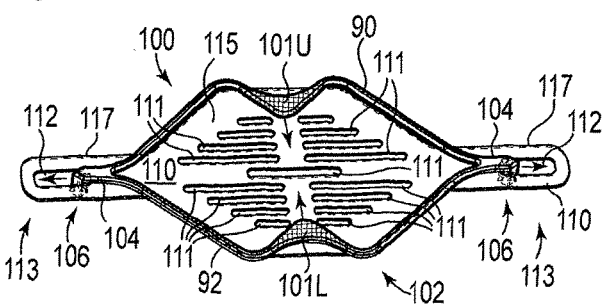
Figure 12:
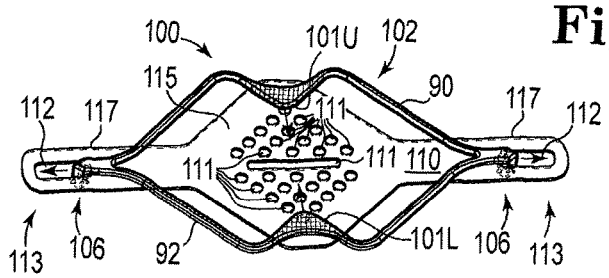

Referring to FIG. 7, indicator 100 includes two opposite ends 104, upper connector 90 having upper cursor (arrow) 101U and spring segment 94; lower connector 92 having lower cursor (arrow) 101L and lower spring segment 96; and center connector 91 having center cursors (or references) 103 and center spring segment 95. Upper cursors (arrows or corners) 101U and lower cursors (arrows or corners) 101L will move relative to center cursor (or reference) (circles or beads) 103, as end segments 104 are moved away from each other (see directional arrows near ends 104).

Tension indicators as featured at FIGS. 1A-1F and 2 through 7 include multiple cursors or a combination of one or more cursors and references, all being embodied on a middle segment or connector of the tension indicator. Alternately, a tension indicator can be useful having just a single location, marking, or structure designated or capable of performing a function of a cursor, e.g., relative to a reference marking (e.g., a color marking or physical structure such as a centerline, arrow, bar, or bead) located on an implant to which the tension indicator is, attached. Relative movement of a single cursor (e.g., a location, marking, color, or structure such as an arrow, angle, bend, kink, curve, point, extension, needle, corner, or bead) on the tension feedback indicator relative to the reference marking on the implant can indicate a tension of an implant material to which the tension indicator is attached.

A tension feedback indicator can be a device having dimensions on a scale of a portion of an implant, e.g., on a scale of an extension portion, and can be sized to be attached to a portion of implant such as along a length of an extension portion. The tension indicator can be made of any material that allows the tension indicator to function as described herein, e.g., by reversibly changing form or shape upon application of tension along a length of the tension indicator and an attached implant, and being able to substantially return to an original shape upon removal of the tension. Useful materials include flexible (non-rigid) polymeric materials such as polyolefin, polyester, nylon, polyurethane, polypropylene, and other similar non-biodegradable or biodegradable polymeric materials known to be useful for preparing surgical devices or instruments. The tension indicator can be formed by any method, such as by standard die cutting or laser cutting of a polymeric film, or by molding a polymeric material into the form of a tension feedback indicator.

A preferred feedback indicator for use with a polypropylene implant material (e.g., polypropylene mesh) can be made from polypropylene film, by laser cutting. By using the same material for the indicator as the implant, a process of joining the indicator to the implant can be simplified, and the indicator can easily be aligned and attached to the implant.

According to certain specific embodiments of tension indicators, an indicator can be used in conjunction with a "backer" or "backer plate" that is located between the tension indicator and an implant to result in improved visualization of the indicator during a surgical procedure. A backer plate can improve visualization of a tension indicator (e.g., a cursor on a tension indicator) by preventing blood, tissue, or other matter from interfering with the function and visualization of the tension feedback indicator (and cursor) attached to an implant. A backer plate can also include a reference (optionally including a scale feature) that allows a visual comparison of a location of a cursor of a tension indicator, to the reference, to assess tension in the implant.

A color contrast between the indicator and the backer (e.g., a cursor and a reference), e.g., provided by a bright background color for the backer (e.g., blue, yellow, or white), allows for better visualization of a cursor of a tension indicator. A backer, e.g., a center or middle of a backer, can also optionally be located at a centerline of an implant to facilitate centering of an implant without a need for a printed centerline marking on the implant itself.

A backer can be attached to an implant on a front surface of an implant between a tension indicator (located also at the front surface) and the implant. A backer can be secured to an implant by use of any attachment mechanism or attachment means that does not interfere with a function of the implant or of the tension indicator. For example, a backer may be placed between the indicator and a front surface of the implant by use of posts or attachment peg located at ends of the tension indicator, that pass through apertures (e.g., two lengthwise elongate apertures or slots) at locations at ends of the backer. The posts extend through the apertures in the backer, while securing arms or ends of the tension indicator to the front face of the implant. The apertures should allow for elongation of the middle segment of the tension indicator and of the implant, without resistance from the backer. The use of an attachment peg (post) secured with a suture on a back side of the implant, through an aperture in the attachment peg (e.g., "suture pinning") allows for simple removal of the tension indicator and backer plate without leaving any portion of these structures remaining, by removal of the suture and then the backer and tension indicator.

A backer plate can preferably self-center behind a tension indicator as the tension indicator extends through a full range of travel. Optionally, as indicated, a reference may include an elongation scale printed or cut into the backer plate to allow objective visual measurement of the length (and elongation) of the indicator, which relates to a tension of the implant.

A backer plate can preferably be constructed of a material having a low surface tension, to assist in working away blood and other fluids to improve visualization of the backer and an adjacent tension indicator. Useful materials include flexible polymeric film materials such as polyolefin, polyester, nylon, polyurethane, polypropylene, Tyvek, and other non-biodegradable or biodegradable polymeric materials. The backer plate can be formed by any method, such as by standard die cutting or laser cutting of a polymeric film, or by molding a polymeric material into the form of a tension feedback indicator.

Size and shape features of a backer plate can be any that will be useful to allow the backer plate to be placed between an implant and a tension indicator on a front side of an extensible implant material, allowing the system (including the implant, tension indicator, and backer) to function as described herein. Various useful design, scale, and style features can be used depending on factors such as the type, size, and use (e.g., therapeutic application) of the implant.

As described and illustrated, a backer can include a reference in the form of structure or indicia that is a fixed part of the backer, which may be in the form of coloration, one or more colored striation, or one or multiple fixed physical structure such as an aperture such as an opening, slot, extension, elongate aperture, or the like, to assist in measuring tension or length of an implant. The reference may be a fixed gauge or demarcation relative to which a cursor of a tension indicator will move during lengthening of the tension indicator and an attached implant.

FIGS. 8 through 13A, 13B, 14A, 14B, 15A, and 15B, illustrate various embodiments of tension indicators 100 and backers 110. Each backer 110 is in the form of a relatively flat polymeric film or plate that can be placed on one side of a tension indicator (100), such as between the tension indicator and a front side of an implant (see FIGS. 13A and 13B, 14A and 14B, and 15A and 15B). Each backer 110 includes two opposing ends 113, a length extending therebetween, a field at surface 115 extending between ends 113, optional references (visual indicia) 111, and optional backer ends or arms 117.

Referring to FIGS. 13A, 13B, 14A, 14B, 15A, and 15B, optional tether (e.g., suture, filament, or wire) 114 can be used to secure the tension indicator to implant material (e.g., mesh) 120. Indicator 100 includes flexible middle segment 102, upper and lower connectors 90 and 92, end portions 104 that can secure tension indicator 100 to an implant in a manner that allows middle segment 102 to be extended and un-extended, and optional attachment posts (pegs) 106 that can be inserted into an aperture of an implant such as a mesh, while also passing through apertures 112 of backer 110. Optionally, but not illustrated at FIGS. 13A, 13B, 14A, 14B, 15A, and 15B, a segment of tether 114 (different from the segment that connects to posts 106) can be connected (e.g., tied, glued, etc.) directly or indirectly (e.g., by use of another tether) to the tension indicator, the backer, or both, to allow tether 114 to be used to remove the tension indicator, backer, or both, from a patient after releasing the tension indicator from the implant by removing tether 114 from the apertures of posts 106.

Another optional feature of a tension feedback indicator and optional backer is a releasable fastener, which is fastener that attaches a tension indicator and (directly or indirectly) backer to an implant for use in a surgical procedure, and allows the tension indicator and optional backer to be easily removed from the implant after placement within a patient. One example of a releasable fastener is at FIGS. 16A, 16B, 16C, 17A, 17B, and 17C, and elsewhere. Alternately, a tension indicator may be non-removable and the indicator and optional backer may be bioresorbable.

Figure 16A:
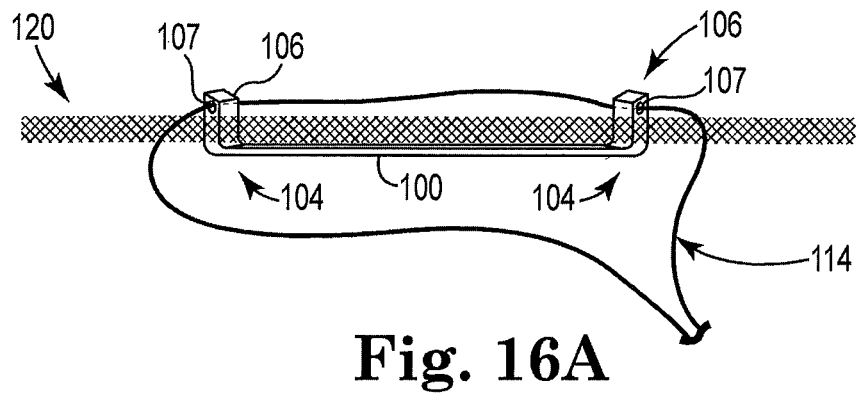
Figure 16B:
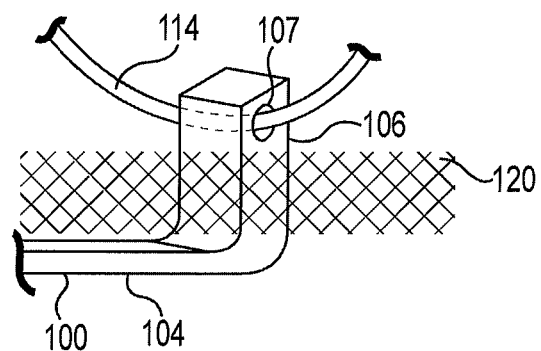

Examples of releasable fasteners include fasteners that include a suture or other tether (which can be removed or pulled out when desired), ultrasonic bonding, thermo-bonding, adhesive bonding, mechanical engagement, a tear-away design using thin film or other bonding methods that allow for a releasable bond, a push-through rivet design that allows ease of assembly and removal, and others. According to certain preferred embodiments, a tension indicator can include two posts (e.g., attachment pegs) at opposite ends of the tension indicator, each post being of a length to extend through the implant from a front side of the implant (at which side the tension indicator is located) to a back side of the implant (at which side the suture attaches to the post by way of a removable engagement). A single suture (optionally also a tether) or equivalent structure such as metal, plastic, polymer (natural or synthetic), wire, thread, or filament, can be attached to each of the two posts by passing through one aperture at a distal location of each post. See, e.g., FIGS. 16A and 16B. Referring to FIGS. 16A and 16B, to remove tension indicator 100 from implant material (e.g., mesh) 120, the single suture (114) can be removed (optionally after cutting) from the two apertures (107) of each post 106, and tension indicator 100 (and optionally a backer plate, if present between indicator 100 and implant material 120) can be removed from implant material (e.g., mesh) 120, previously surgically placed.

A fastener or attachment mechanism can be made in any form and from any material that allows a tension indicator to be secured as desired (permanently or removably) to an implant. A material can be as desired, including a material as described herein for use in a tension indicator, backer, or an implant. In certain embodiments polypropylene may be a useful material for bonding techniques such as ultrasonic welding and heat staking, especially with an implant material made of polypropylene mesh. Alternate attachment mechanisms or fasteners can include mechanical structures such as rivets or pegs (or "extensions" or "standoffs") that can be pushed through an existing aperture (e.g., a pore of a mesh, or an aperture of a molded implant material) of an implant material in a manner to permanently or removably secure a tension indicator to an implant (and optional backer) without additional processing. As specified, an exemplary design that can be used is a post-suture design that uses an attachment peg (post) extending from the indicator. The attachment peg passes through the thickness of the implant material and a suture is used as a pin passing through an aperture at the distal end of the peg, on the side (the back side) of the mesh opposite of the indicator (which is located on the front side) so the suture acts as a cotter pin to secure the tension indicator in place during use. The backer is located and held in place between the implant material and the indicator. After surgical placement of the implant in a patient, the suture can be removed to allow the tension indicator and optional backer to be removed.

FIGS. 16A, 16B, 16C, 17A, 17B, 17C, 17D, 17E, and 17F illustrate embodiments of tension feedback indicators 100 with attachment peg or alternate attachment structure (fastener) 106. In certain embodiments attachment structure 106 is a rivet or other mechanical fastener. In other embodiments attachment structure 106 includes an aperture at a distal end through which a suture (e.g., a tether 114) extends to releasably (non-permanently) secure attachment structure 106 and indicator 100 to an implant material (e.g., a mesh) 120. Indicator 100 include a flexible middle segment 102, two end portions 104 for securing to an implant, and optional attachment posts (pegs) 106 (or other attachment structure) that can be inserted into an aperture of an implant such as a mesh, while also passing through apertures 112 of backer 110.

Figure 16C:
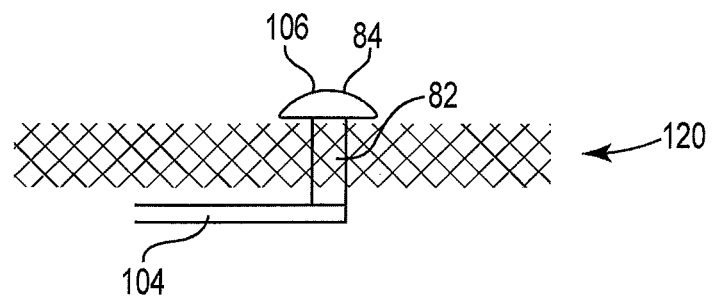

Referring to FIGS. 16C, 17A, and 17B, these illustrate embodiments of fasteners 106 in the form of polymeric rivets having shaft 82 that extends through a thickness of implant material (e.g., mesh) 120, and an expanded rivet head 84 on a back side of implant material 120. Fastener (rivet) 106 is attached at one side of implant material 120 to arm 104 of tension indicator 100 (this may be referred to as the "base" of a post-type fastener 106 as illustrated). Fastener (rivet) 106 passes from a front side of implant material 120 (the side on which arm 104 also resides), through a thickness of material 120, and to a back side, at which side an expanded "rivet head" at a distal end of fastener (rivet) 106 holds fastener 106 within an aperture of material 120. Fastener (rivet) 106 may be permanent, meaning that fastener 106 may not be manually removed from material 120, or may be removable, meaning that a surgeon may manually pass the expanded rivet head 84 through the aperture of material 120 and back to the front side of material 120 to manually release tension indicator 100 from material 120, e.g., during a surgical procedure.

FIGS. 17C and 17D show a similar embodiment and additionally show the polymeric rivet fastener during placement at material 120. In specific, FIG. 17C shows fastener 106 having shaft 82 and a distal end that has not yet been formed into an expanded rivet head (84). FIG. 17D shows fastener 106 of FIG. 17C, after the distal end has been processed into expanded rivet head 84.

FIGS. 17E and 17F show other alternate embodiments of a fastener between an arm 104 of a tension indicator (not shown) and an implant material (e.g., mesh) (120). As illustrated, arm 104 can be made of a flexible polymeric film material that can be threaded from a front side of mesh 120, through one or more, apertures of mesh 120, to exit again at the front side of mesh 120 where arm 104 is bonded to itself by adhesive or heat bonding. In still alternate versions, an arm 104 can be directly bonded by heat bonding, adhesive, etc., to material 120.

A useful, optional feature of embodiments of implants as described and illustrated herein can be an attachment between the implant and the tension indicator and optional backer that allows for quick and convenient removal of a tension feedback indicator and backer from the implant (e.g., a releasable fastener). Certain releasable fasteners can be manipulated easily using a standard surgical tool or instrument. Preferred releasable fasteners can include a suture that, at one segment, secures the tension indicator to the implant material, and at another segment includes a loop, knot, or other connection to the tension feedback indicator, backer, or both. In use the implant can be placed and adjusted. Then the tether (e.g., suture or equivalent) can be pulled at a knot, length, loop, or other easily identifiable structure of the tether to release the tension feedback indicator and optional backer from the implant. Optionally, the tension feedback indicator, backer, or both, can be secured to the tether so that removing the tether from the implant and patient also results in removal of the tension feedback indicator, backer, or both from the implant and patient to leave only the implant remaining in the patient. Advantageously, these systems can allow simple and quick removal of the tension feedback indicator and optional backer, for intra-operative purposes.

FIG. 18 shows an embodiment of tension indicator 100, including posts 106 that are capable of extending through apertures (not shown) of an implant material. Posts 106 have a length extending from a base of the post connected at arm 104, a distance that approximates a thickness of an implant material 120 (not shown). Optionally, in embodiments of implants that also include a backer (not shown) located between a tension indicator and a front side of an implant material, posts 106 can also extend loosely through apertures of the backer. When releasably secured to material 120, tension indicator 100 resides on a front side of an implant (e.g., material 120), and apertures 107 reside on a back side. Segments 114B and 114C of suture 114 extend through apertures 107 and act as pins that maintain the position of tensioner 100 against an implant. In use, end 114A of tether (e.g., suture) 114 can be pulled away from tension indicator 100, such that segments 114B and 114C are drawn in the direction of the arrows (see FIG. 18). After the loose end 115 of passes through both apertures 107 of both posts 106, suture 115 can be drawn entirely away from tension indicator. Then, after removal of tether 114 from apertures 107, fasteners 106 can be freely released from apertures of the mesh material and tension indicator 100 and an optional backer can be removed from the implant material 120.

Still referring to FIG. 18, optionally (but not shown), one or more segment of tether 114 can be attached to tension indicator 100 and an optional backer on a front side of an implant. Accordingly, after removing segments 114B and 114C from both apertures 107, the attached segment (e.g., 114F) remains attached to tension indicator 100 and the optional backer. Upon removing tension indicator 100 from implant material 120, tension indicator 100 and the optional backer remain attached to tether 114 at segment 114F and can be also carried away from implant material 120 with tether 114.

Figure 19A:
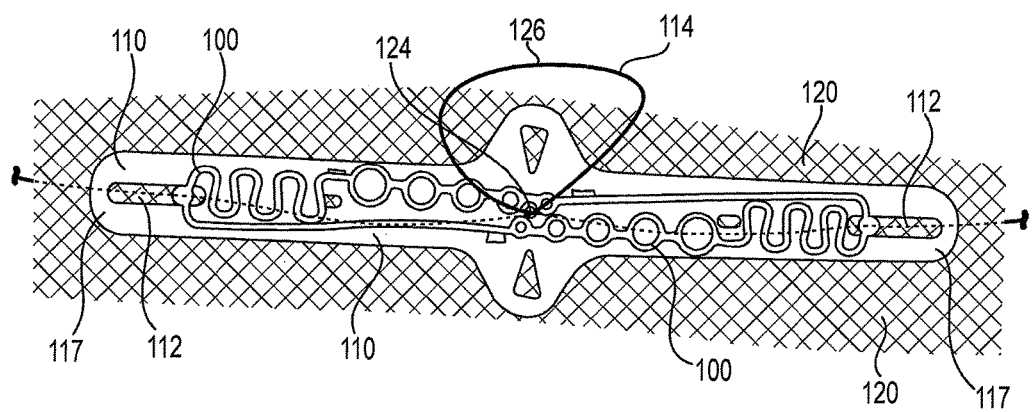
FIGS. 19A, 19B, and 19C illustrate an embodiment of an implant.

FIGS. 19A (top view), 19B (bottom view), and 19C (side view), show another embodiment of an implant that includes a backer (110), tension indicator (100), implant material (120), and tether (114). As illustrated, backer 110 is located on a front side of implant material 120 between tension indicator 100 and implant material 120. Posts 106 extend through apertures 112 of backer 110, through a thickness of implant material 120, and to a back side. Each distal end of posts 106 includes an aperture through which a segment of tether 114 is threaded to act as a pin of the releasable fastener. Tether 114 is also threaded from the back (bottom) side of implant material 120 through implant material 120 and through a central aperture 124 of backer 110. On the front side of the implant (the same side as the locations of backer 110 and tension indicator 100), tether 114 forms loop 126. Tether 114 is loosely threaded through aperture 124, and also through the apertures at ends of posts 106. As a result, tether 114 (at loop 126 on the front side of the implant) can be pulled in a direction away from implant material 120 (see arrow at FIG. 19C) to cause tether 114 to be pulled through and out of the apertures of posts 106 and through and out of central aperture 124 of backer 110, to be separated from backer 110, tension indicator 100, and implant material 120. Upon such removal of tether 114, posts 106 are allowed to be removed from their placement in the apertures of implant material 120, and backer 110 and tension indicator 100 can be displaced and removed from the implant and implant material 120.

In use, upon placement of the implant in a patient to support tissue, tension indicator 100 can be used in conjunction with backer 110 to monitor or identify a tension within implant material 120. Upon successful placement of the implant, suture 114 can be pulled in a direction away from implant material 120 (see arrow at FIG. 19C) to separate suture 114 from each of backer 110, tension indicator 110, and implant material 120. Backer 110 and tension indicator 110 can then be removed from implant material 120 and the patient.

Figure 19B:
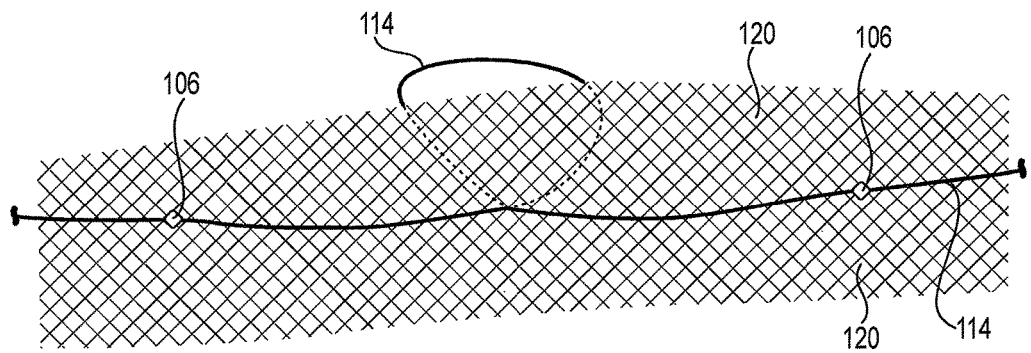
Figure 19C:
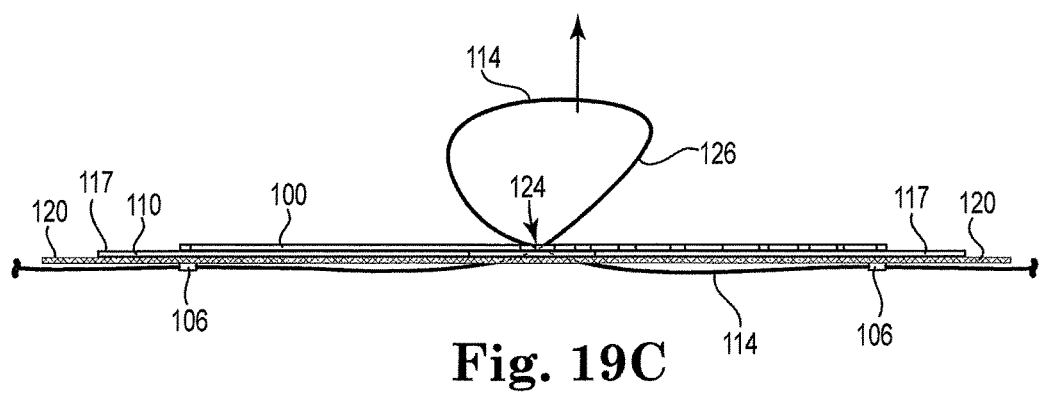
Figure 20A:
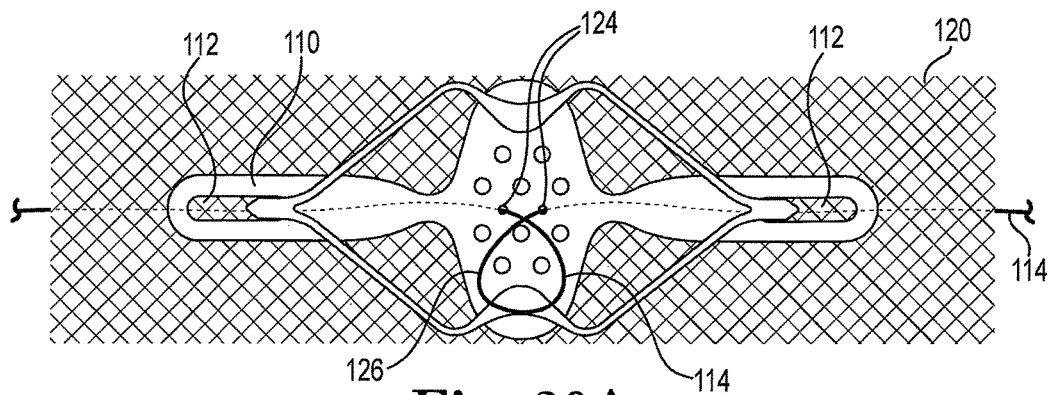
FIGS. 20A and 20B illustrate an embodiment of an implant.
Figure 20B:
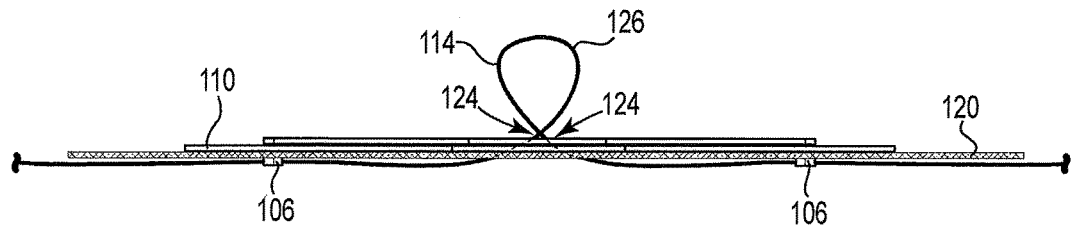
Figure 21A:
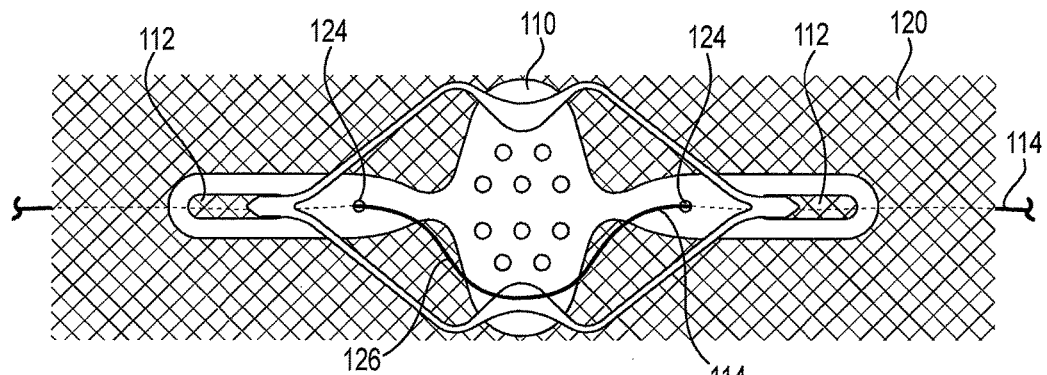
FIGS. 21A and 21B illustrate an embodiment of an implant.
Figure 21B:
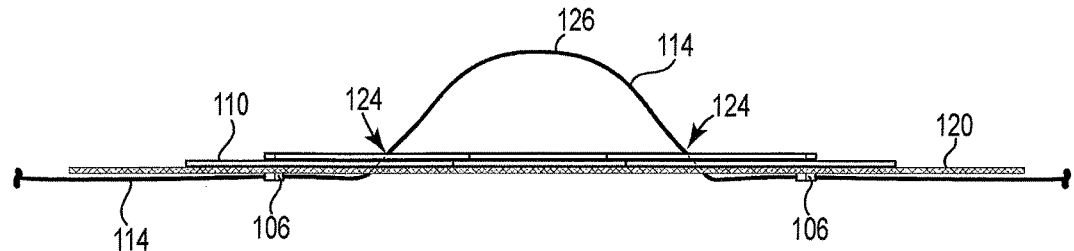

FIGS. 20A and 20B show an implant that includes a combination of implant material, tension indicator, backer, and tether, similar to FIGS. 19A, 19B, and 19C, with alternate designs of the tension indicator and backer, and alternate placement of apertures 124. Likewise for FIGS. 21A and 21B, which also includes an alternate loop 126 and alternately-located apertures 124.

Figure 22A:
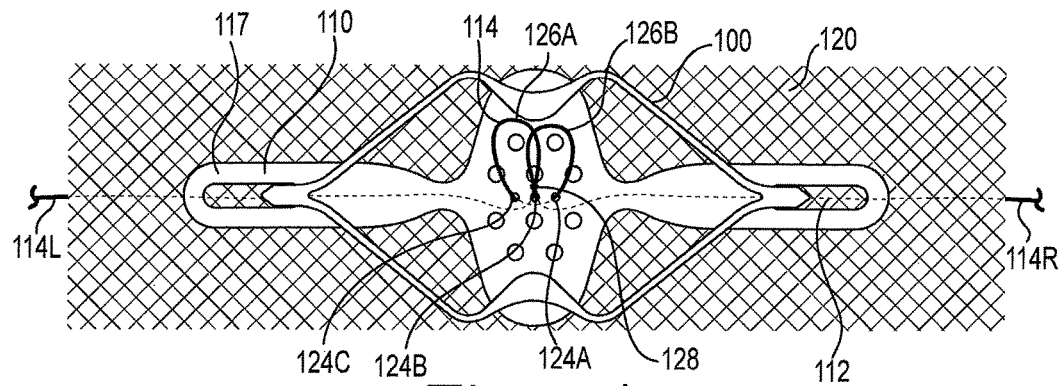
FIGS. 22A and 22B illustrate an embodiment of an implant.
Figure 22B:
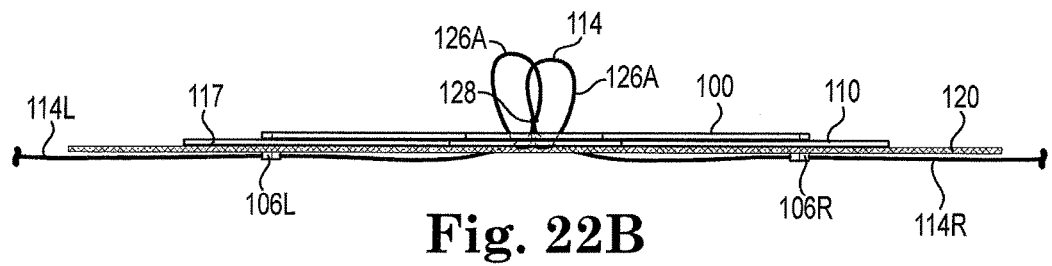

FIGS. 22A and 22B show an implant that includes a combination of implant material, tension indicator, backer, and tether, similar to FIGS. 19A, 19B, and 19C, with alternate designs of the tension indicator and backer, and alternate threading of suture 114 of backer 110. As shown at FIGS. 22A and 22B, tether 114 extends from post 106R along a back side of implant material 120, through material 120, to a front side of material 120, then through aperture 124B (a center aperture, between apertures 124A and 124C). Tether 114 continues to form loop 126B on a front side of implant material 120, and then passes in the opposite direction through aperture 124A. Tether 114 then extends underneath the backer but still on the front side of material 120, i.e., between backer 110 and the front side of material 120, to pass through aperture 124C from the backside of backer 110 to the front side of backer 110. Tether 114 forms loop 126A on the front side of the implant, is tied at knot 128 to loop 126B, passes again through aperture 124B, through material 120 to the back side of material 120, then along a length of the back side of material 120 to and through an aperture in the other post 106L.

Upon successful placement of the implant, suture 114 can be manipulated to disengage backer 110 and indicator 100 from implant material 120, and then to assist in removing backer 110 and indicator 100 from implant material 120 and out of the patient. A surgeon may grasp knot 128 and pull the knot in a direction away from the front side of the implant. This will pull tether segments 114L and 114R away from and through apertures in their respective posts 106L and 106R A short segment of tether 114 will remain in a back side of backer 110 between apertures 124C and 124A. Accordingly, removal of tether 114 from the patient will also carry along with the tether, backer 110, and indicator 100.

Figure 23A:
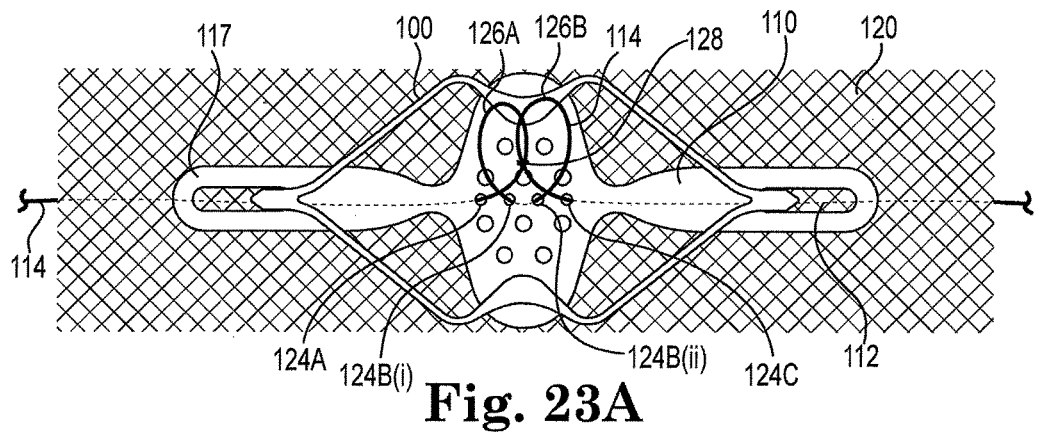
FIGS. 23A and 23B illustrate an embodiment of an implant.
Figure 23B:
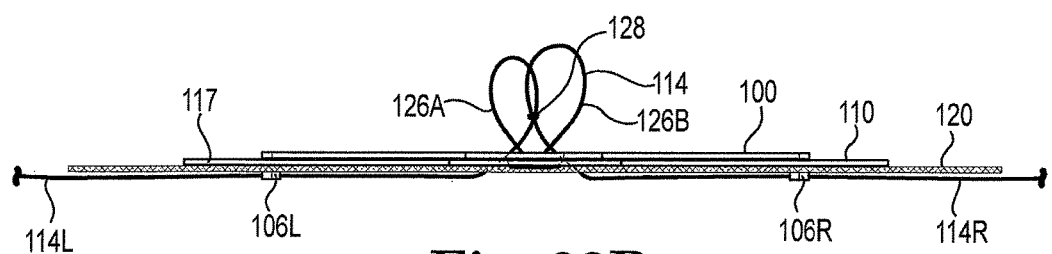

The system of FIGS. 23A and 23B is similar, with an altered tether arrangement. Tether 114 extends from post 106R along a back side of implant material 120, through material 120, to a front side of material 120, then through aperture 124C. Tether 114 forms loop 126B on a front side of implant material 120 and then passes in the opposite direction through aperture 124B(ii). Tether 114 then extends underneath the backer but still on the front side of material 120, i.e., between backer 110 and the front side of material 120, to pass through aperture 124B(i) from the backside of backer 110 to the front side of backer 110. Tether 114 forms loop 126A on the front side of the implant, is tied at knot 128 to loop 126B, passes through aperture 124A, through material 120 to the back side of material 120, then along a length of the back side of material 120 to and through an aperture in the other post 106.

Upon successful placement of the implant, suture 114 can be manipulated to disengage backer 110 and indicator 100 from mesh material 120, and then to assist in removing backer 110 and indicator 100 from implant material 120 and the patient, in the same manner as described for the embodiment of FIGS. 22A and 22B.

Figure 24A:
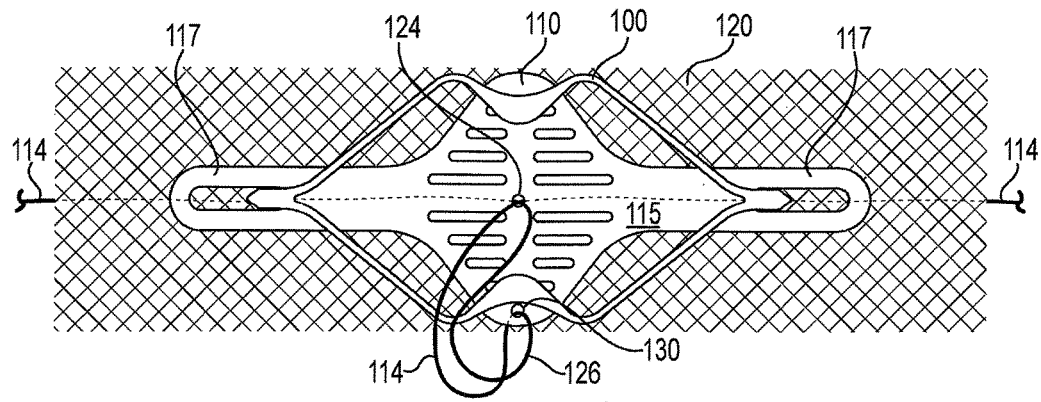
FIGS. 24A and 24B illustrate an embodiment of an implant.
Figure 24B:
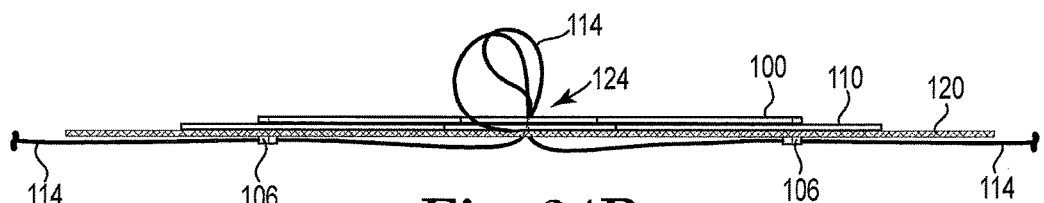

FIGS. 24A and 24B show a system that includes certain features in common with the system of FIG. 19A. A feature of the embodiment at FIGS. 24A and 24B is that loop 126 extends through peripheral aperture 130 of backer 110 (at that location, the loop does not pass through implant material 120). The location of aperture 130 can vary as desired and can be placed at a location of field 115 or an arm 117. In use, upon placement of the implant, the segments of tether 114 located on the back side of the implant and through apertures of posts 106 can be withdrawn by pulling those segments to the front side of the implant, through aperture 124. Upon such withdrawal, loop 126 will remain extended through aperture 130, allowing for tether 114 to be withdrawn from the patient in a manner that will carry backer 110 (and preferably indicator 100, not directly attached to tether 114) along with tether 114.

Figure 25A:
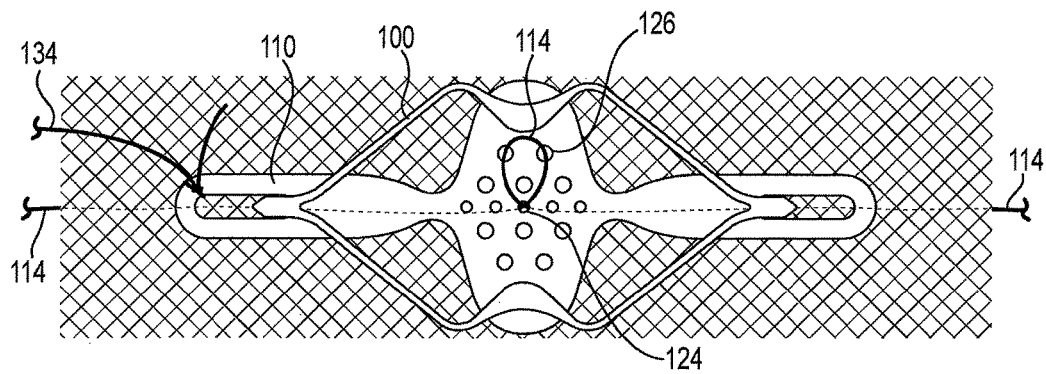
FIGS. 25A and 25B illustrate an embodiment of an implant.
Figure 25B:
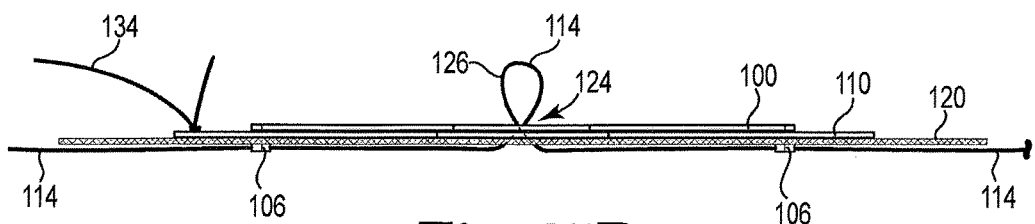

FIGS. 25A and 25B show a system that includes certain features in common with the system of FIG. 19A. A feature of the embodiment at FIGS. 25A and 25B is as second tether (e.g., suture) 134, attached to backer 110. The attachment may be by a knot, adhesive, or otherwise. Tether 134 is shown to be attached at arm 117 but could be attached at any location. In use, loop 126 can be pulled to release tether 114 from posts 106. Tether 134, attached to backer 110, can be manipulated to carry backer 110 (and preferably indicator 100, not directly attached to tether 114) away from implant material 120 and out of a patient.

Figure 26A:
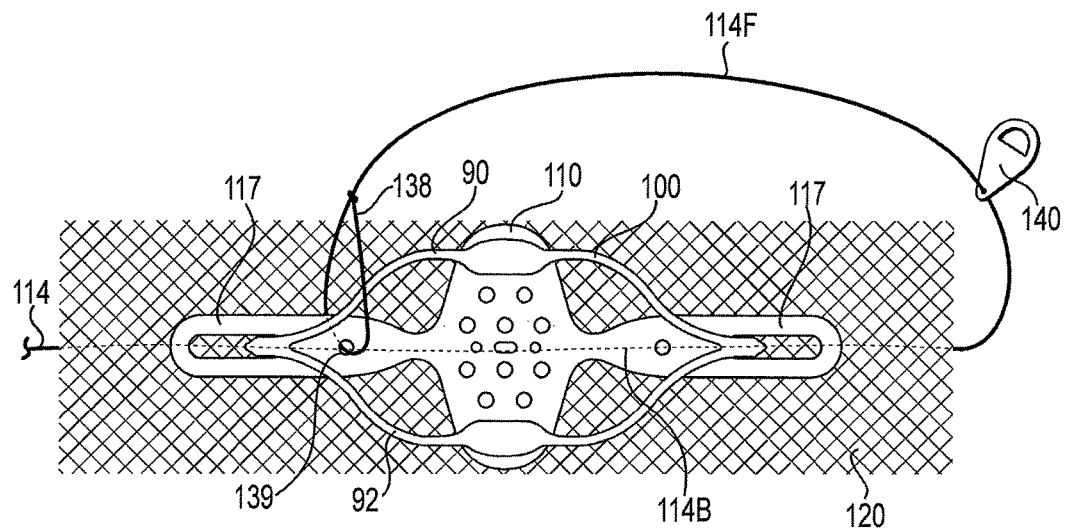
FIGS. 26A and 26B illustrate an embodiment of an implant.
Figure 26B:
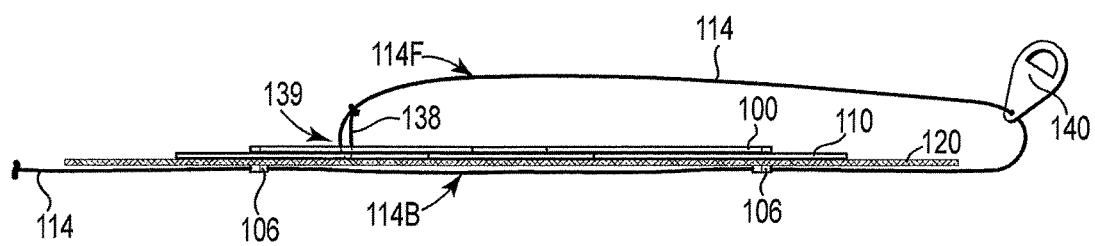

FIGS. 26A and 26B show a system that includes certain features in common with the system of some of the previous figure, including implant material 120, indicator 100, backer 110, tether 114, and other features as indicated by common numerical designations. A back side segment 114B of tether 114 extends on a back side of the implant through apertures of posts 106, as pins, keeping posts 106 in place through apertures of material 120. Apertures of posts 106 extend through posts 106 in a direction aligned with a length of implant material 120 (alternately, the apertures could align with a width direction of implant material 120). Another segment of tether 114, front side segment 114F, is located on the front side of the implant and includes loop 138 that attaches to backer 110 through aperture 139, and also attached to indicator 100 by extending around connector 90. The attachment is shown to be by a loop, but may alternately be any another attachment configuration such as one or more knot, adhesive, or otherwise. Aperture 139 is shown to be located at or near arm 117 but could be at any useful location. In use, tab 140 (attached to suture 114) can be pulled to release back side segment 114B from posts 106, to release backer 110 and indicator 100 from material 120. Tether 114 then can be manipulated to carry backer 110 and indicator 100 away from implant material 120 and out of a patient.

Figure 27A:
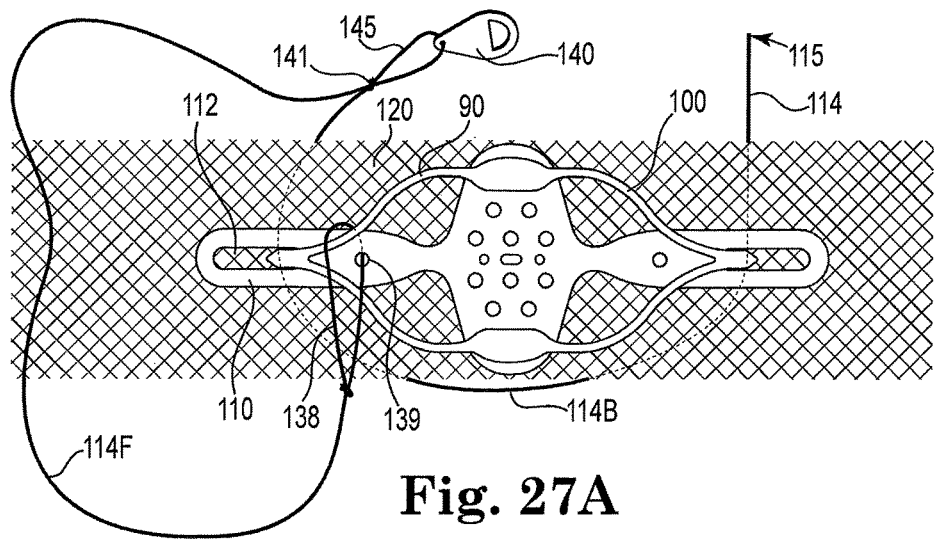
FIGS. 27A, 27B, and 27C illustrate embodiments of implants.
Figure 27B:
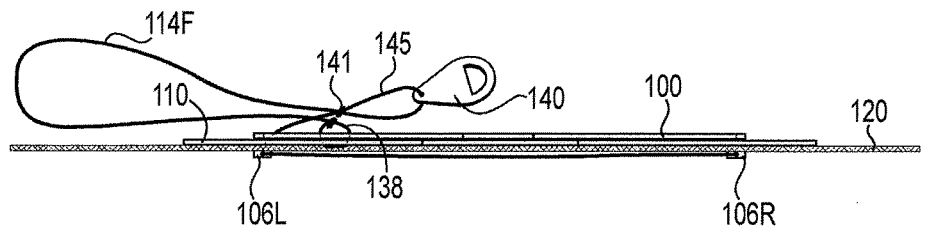

FIGS. 27A and 27B show a system that includes certain features in common with the system of FIGS. 26A and 26B. As shown, knot 141 is located along the length of tether 114 to define loop 145 that secures tab 140 to tether 114. A back side segment 114B of tether 114 extends on a back side of the implant through apertures of posts 106, as pins, keeping posts 106 in place through apertures of material 120. Apertures (not shown) of posts 106 extend through posts 106 in a direction aligned with a width of implant material 120. Another segment of tether 114, front side segment 114F, is located on the front side of the implant and includes loop 138 that attaches to backer 110 through aperture 139, and also attached to indicator 100 by extending around connector 90.

Still referring to FIGS. 27A and 27B, a length of back side segment 114B that is required to be drawn to disengages posts 106 is shorter than the length of front side segment 114F. For purposes of defining these lengths, the length of back side segment 114B can be considered to be the length of tether 114 between left post 106L and end 115. The length of front side segment 114F can be considered to be the length of tether 114 between knot 141 and loop 138 passing through aperture 139. In use, tab 140 can be pulled, causing segment 114B and loose end 115 to be drawn through and become disengaged from both of the apertures of posts 106L and 106R. Because the operable length of segment 114B is shorter than the length of segment 114F, segment 114B will become disengaged from the apertures of both posts 106R (first) and 106L (second) to release backer 110 and indicator 100 from material 120, while slack still remains in segment 114F. Thereafter, tab 140 can be pulled farther from the implant to remove the slack from segment 114F, then still farther to carry backer 110 and indicator 100 away from implant material 120 and out of the patient.

Figure 27C:
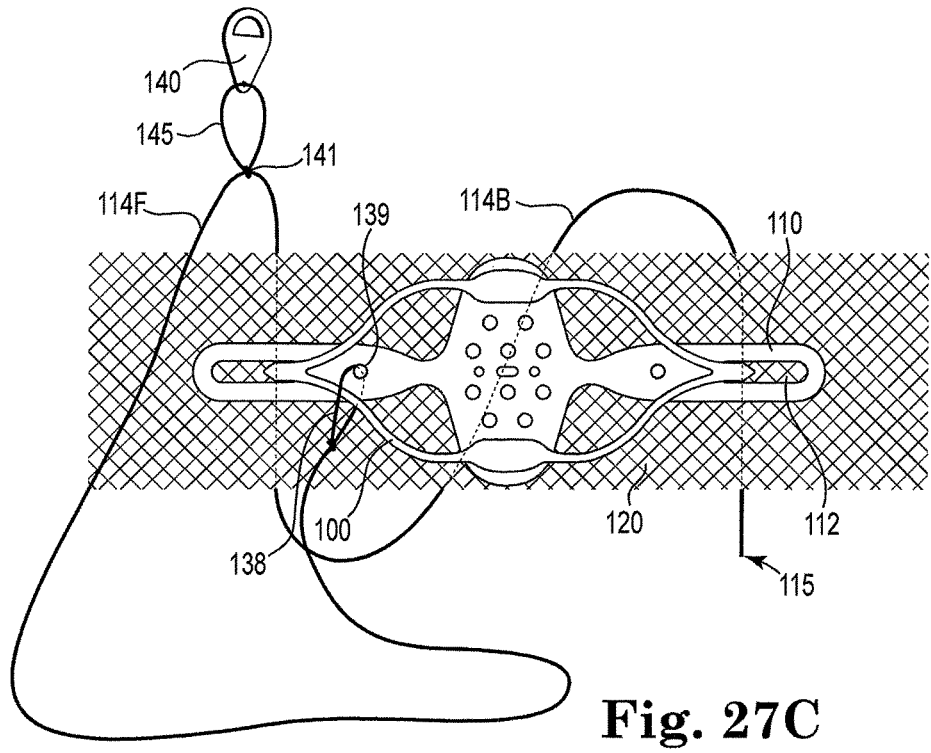

The system of FIG. 27C is similar to the system of FIGS. 27A and 27B except that back segment 114B is threaded through the apertures of posts 106 in a different manner. As with the system of FIGS. 27A and 27B, the apertures (not shown) of posts 106 extend through posts 106 in a direction aligned with a width of implant material 120. But segment 114B is passed through the apertures in directions that differ from the directions of passage of segment 114B through the apertures of the system of FIGS. 27A and 27B. Whereas segment 114B of the system of FIGS. 27A and 27B extends from "top to bottom" (using knot 141 as a starting point and end 115 as an end point) through the aperture of left post 106L (as illustrated at FIG. 27A) and then from "bottom to top" through the aperture of right post 106R, segment 114B of the system of FIG. 27C is passed from "top to bottom" (using knot 141 as a starting point and end 115 as an end point) through the aperture of the left post (as illustrated at FIG. 27B) and then again from "top to bottom" through the aperture of the right post.

Figure 28A:
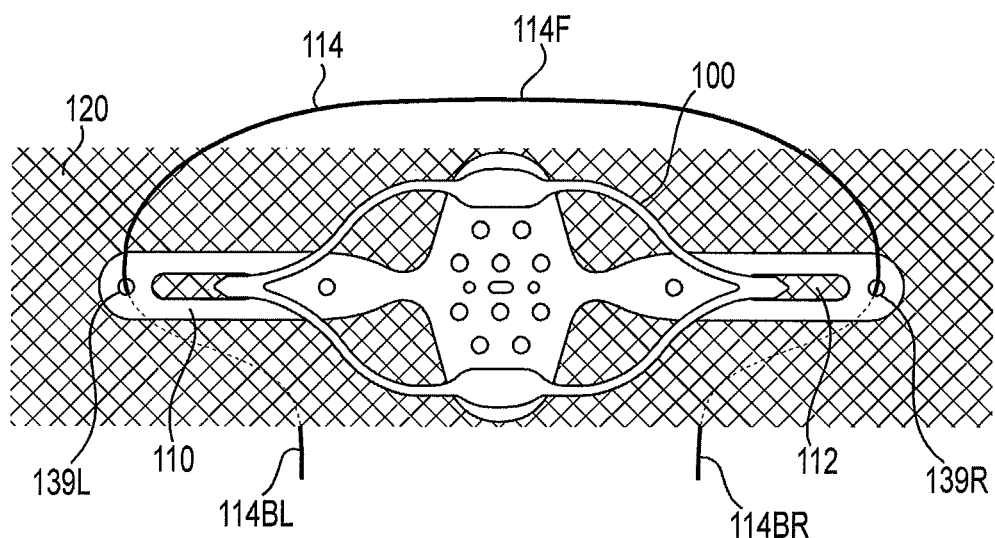
FIGS. 28A and 28B illustrate an embodiment of an implant.
Figure 28B:
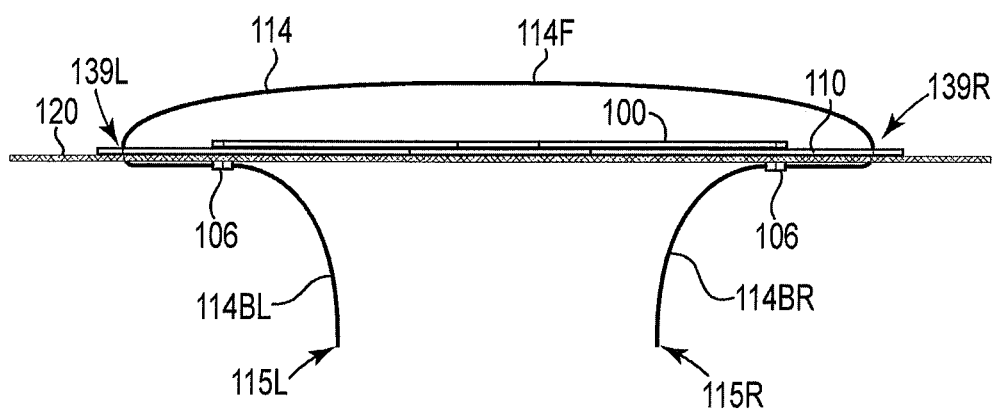

FIGS. 28A and 28B show a system that includes certain features in common with the system of some of the previous figures, including implant material 120, indicator 100, backer 110, and tether 114. Backer 110 includes apertures 139L and 139R at far distal ends of arms 117. Tether 114 includes a front segment 114F that extends on the front side of implant material 120, backer 110, and indicator 100. Front segment 114F extends in one direction through aperture 139R on a first (right) end of backer 110, and in a second direction through aperture 139L at a second (left) end of backer 110. Tether 114 includes two back segments 114BR and 114BL. Each back segment extends through an aperture (not shown) of a post 106 and then each ends at an end 115R and 115L. In use, a location along front segment 114F can be pulled away from implant material 120 to release back side segments 114BL and 114BR from their respective posts 106, to release backer 110 and indicator 100 from material 120. As illustrated, tether 114 is not attached to either backer 110 or indicator 100. Optionally, tether 114 could also be attached to backer 110, indicator 100, or both, e.g., through another tether (e.g., a connective tether).

Figure 29A:
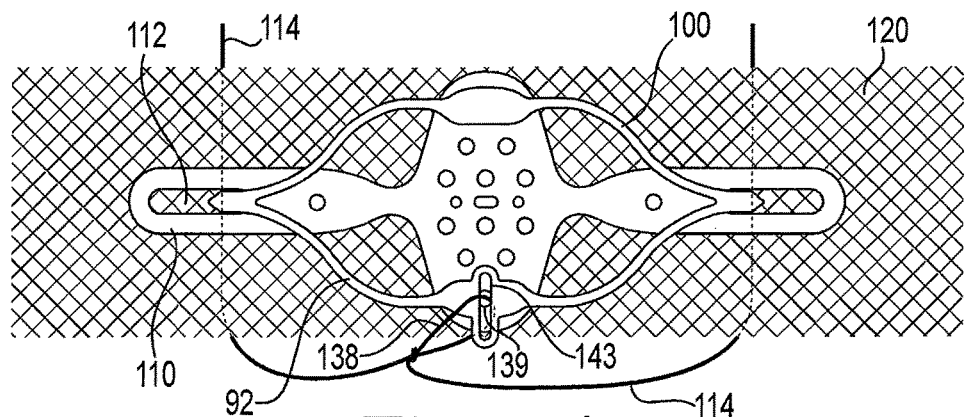
FIGS. 29A and 29B illustrate an embodiment of an implant.
Figure 29B:
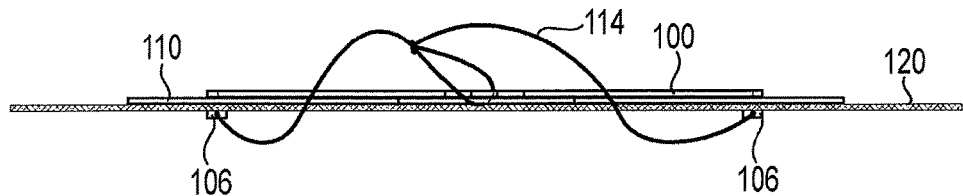

FIGS. 29A and 29B show a system that includes certain features in common with the system of some of the previous figures, e.g., 28A and 28B, including implant material 120, indicator 100, backer 110, and tether 114. Backer 110 includes aperture 139 located at a medial location and behind lower connector 92. Lower connector 92 includes aperture 143 in the form of a vertical elongate slot, which allows lower connector 92 to move vertically without inhibition from loop 138 of tether 114 passing through aperture 143 and aperture 139 of backer 110. Loop 138 of tether 114 connects to backer 110 and tensioner 100 at apertures 139 and 143, respectively. Loop 138 does not pass through implant material 120 at this location. Two ends of tether 114 then extend away from loop 138 in each of a right and a left direction, through apertures (extending in a width direction) in posts 106 on a backside of implant material 120. In use, each of the two segments of tether 114 that extends through an aperture of the posts 106 can be pulled away from each post 106 to release each of those segments from its respective post 106, to release backer 110 and indicator 100 from material 120. Thereafter, any portion of tether 114 can be pulled from the implant to carry backer 110 and indicator 100 away from implant material 120 and out of a patient.

Figure 30A:
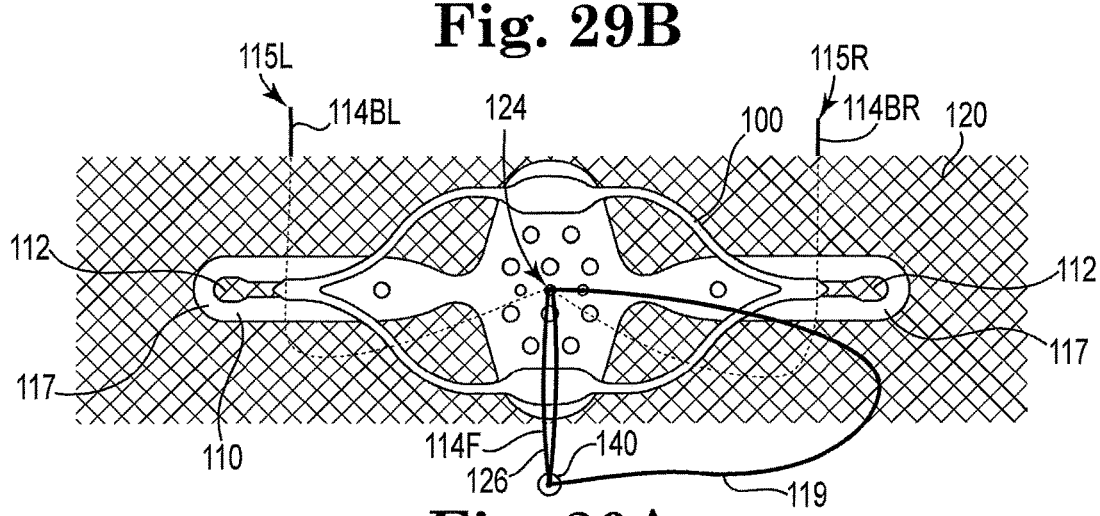
FIGS. 30A and 30B illustrate an embodiment of an implant.
Figure 30B:
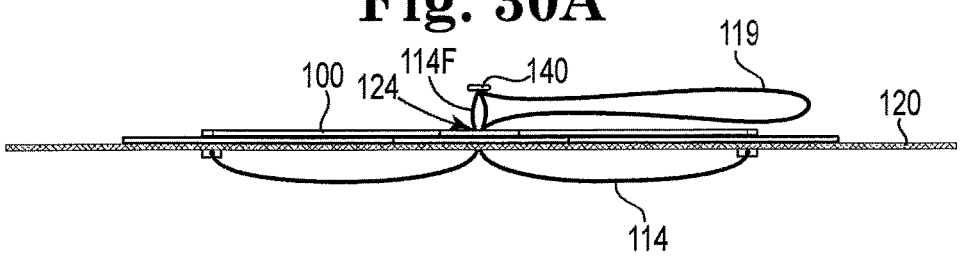

FIGS. 30A and 30B show a system that includes certain features in common with the system of FIGS. 25A and 25B, and others, as shown for example by commonly numbered features. A feature of the embodiment at FIGS. 30A and 30B is a second tether (e.g., a connecting tether) 119, attached at a first end to tab 140, and at a second end to backer 110. Tab 140 also attaches to loop 126 of segment 114F of tether 114. As illustrated, the second end of second tether 119 is connected to backer 110 at or near aperture 124, but could be attached at any other location, and could also optionally be attached to indicator 100. Any of the attachments may be by a knot, adhesive, or otherwise. A front segment 114F of tether 114 forms loop 126 on a front side of the implant. Back segments 114BR and 114BL extend through aperture 124 and implant material 120, exiting on the bottom or back side of implant material 120 and then extending each in a left or a right direction to and through an aperture of post 106, ending at end 115R and 115L. In use, tab 140 can be pulled to pull distal portions of segments 114BR and 114BL through posts 106, releasing those segments from the posts. Segments 114BR and 114BL will become disengaged from the apertures of both posts 106 to release backer 110 and indicator 100 from material 120, while slack still remains in second tether 119. The length of each portion of segments 114BR and 114BL extending from a post 106 and a loose end 115 (L, R) is shorter than the length of second tether 119 between aperture 124 and tab 140. Tab 140 can be pulled farther from the implant to remove the slack from second tether 119, then still farther to carry backer 110 and indicator 100 away from implant material 120 and out of the patient. As illustrated, second tether 119 is not attached to indicator 100, but second tether 119 can optionally be attached to an indicator.

Also shown at FIG. 30A is an optional feature of backer 110 at each aperture 112 of the two arms 117. As shown, apertures 112 are elongate slots extending in a length-wise direction. Each aperture 112 is of a non-uniform width. Each aperture has a more narrow (reduced) width at the more medial (inboard) end of the aperture or slot, and a wider (greater) width at the far opposed (outboard) ends. Each post 106 extending through the apertures 112 of non-uniform width may exhibit a dimension to accommodate the reduced width, to allow the post to extend along the entire length of elongate slot 112 as indicator 100 is lengthened or reduced in its length dimension. This reduced dimension of the post may be a slot or portion at or near the "base" of the post 106, near the connection of post 106 to tensioner 100. A post 106 may also exhibit a larger dimension, e.g., at a distal end of the post, the larger dimension being of a size that can pass through the wider (greater) width of aperture 112 but that is also larger than the narrow (reduced) width of aperture 112.

Figure 31A:
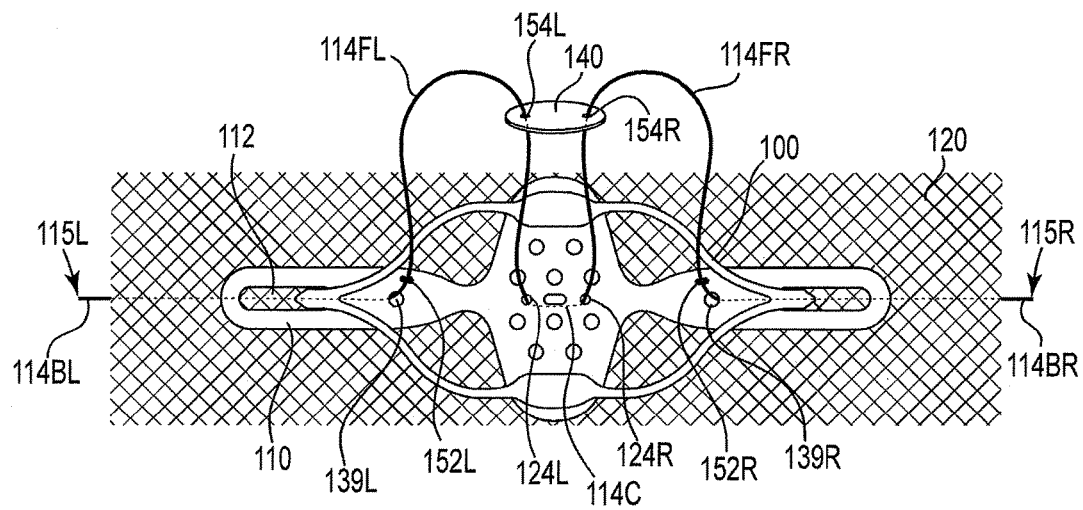
FIGS. 31A and 31B illustrate an embodiment of an implant.
Figure 31B:
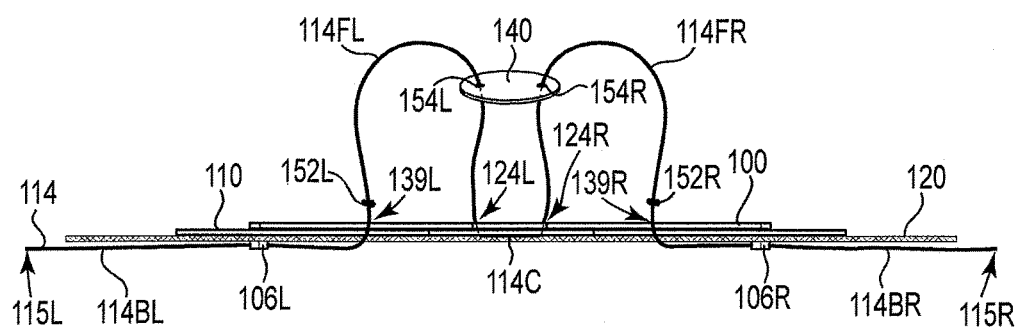
Figure 32A:
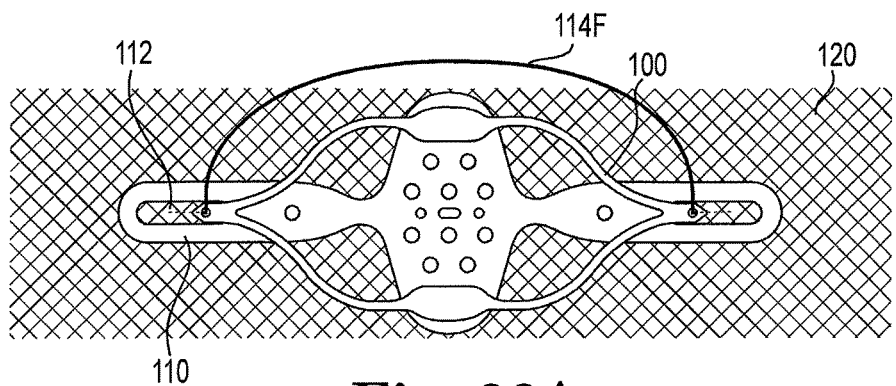
FIGS. 32A, 32B, 32C, and 32D illustrate embodiments of implants.
Figure 32B:
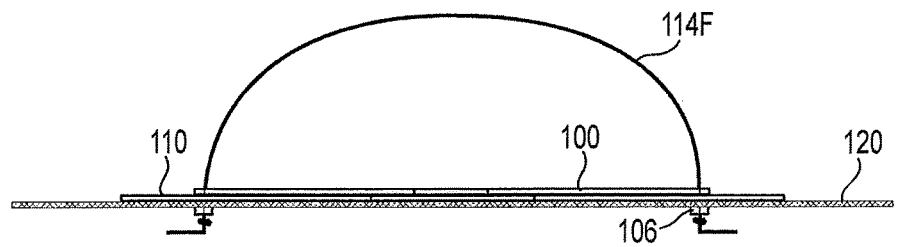
Figure 32C:
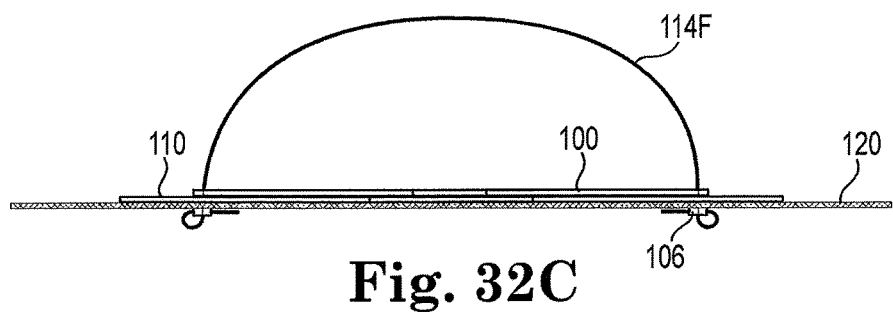
Figure 32D:
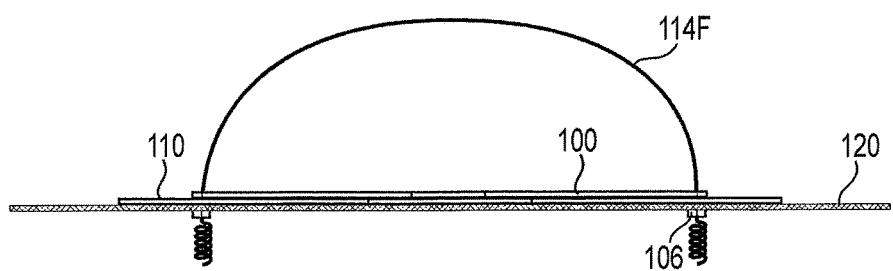

FIGS. 31A and 31B show a system that includes certain features in common with other system, as shown for example by commonly numbered features. Tether 114 includes multiple segments. Segment 114BL extends from end 115L to an aperture of post 106L. Segment 114BR extends from end 115R to an aperture of post 106R. Segment 114FL extends from stopper 152L to aperture 154L of tab 140. Segment 114FR extends from stopper 152R to aperture 154R of tab 140. Segments 114BL and 114BR are shorter than segments 114FL and 114FR. In use, tab 140 can be pulled away from the implant to pull segments 114BR and 114BL through posts 106, releasing those segments from the posts. Segments 114BR and 114BL will become disengaged from the apertures of both posts 106 to release backer 110 and indicator 100 from material 120, while slack still remains in segments 114FL and 114FR. After ends 115L and 115R have passed through the apertures of posts 106, stoppers 152L and 152R engage tab 140 at apertures 154L and 154R and are too large to pass through apertures 154L and 154R. Tab 140 can be pulled farther from the implant to remove the slack from segments 114FL and 114FR, then still farther to carry backer 110 and indicator 100 away from implant material 120 and out of a patient.

FIGS. 32A, 32B, 32C, and 32D show systems that include features in common with other described systems as shown for example by commonly numbered features. Different from other systems, posts 106 of these systems include an aperture that extends through each post in a direction extending from the front side of the implant to the back side, i.e., longitudinally along the length of each post extending from the front side of implant material 120 to the back side of implant material 120, or through the thickness of the implant material. In each system, tether 114 includes a front loop extending on the front side of the implant between the two posts at opposing ends of indicator 100. The tether extends through the aperture in each post 106. Each post extends through the thickness of the implant material 120. Each tether extends distally or longitudinally out the distal end of a post. On the back or bottom side of the implant each tether includes an obstruction that prevents the tether from easily passing back through the aperture, such as by manually pulling on segment 114F. The obstruction may be a bend or kink in the tether (e.g., FIG. 32B), a melted component of a polymeric suture or other material attached to or formed in the tether (e.g., FIG. 32B), a curved tether optionally passed through another aperture in the post (e.g., FIG. 32C), a corkscrew, or any other wound, kinked, bent, or otherwise shaped length of tether. In use, each obstruction will not pass back through the aperture of the post by manually pulling on segment 114F. But, each obstruction is sufficiently small or sufficiently conformable to pass through an aperture of the implant material by manually pulling on segment 114F. After the implant is placed as desired in a patient, the surgeon can pull on segment 114F, causing indicator 100 to be separated from implant material 100 due to traction on tether 114 at posts 106. As illustrated, tether 114 is not attached to backer 110, but can optionally be attached directly or indirectly to backer 110, e.g., by use of a second tether.

Figure 33A:
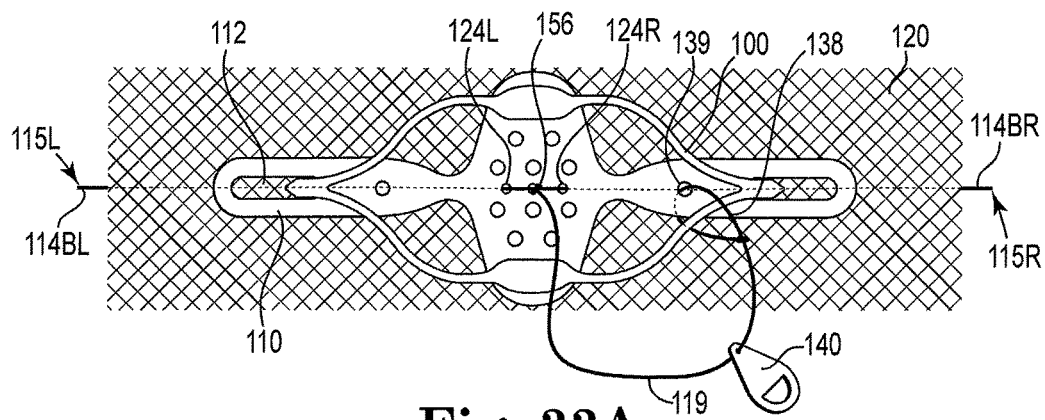
FIGS. 33A and 33B illustrate an embodiment of an implant.
Figure 33B:
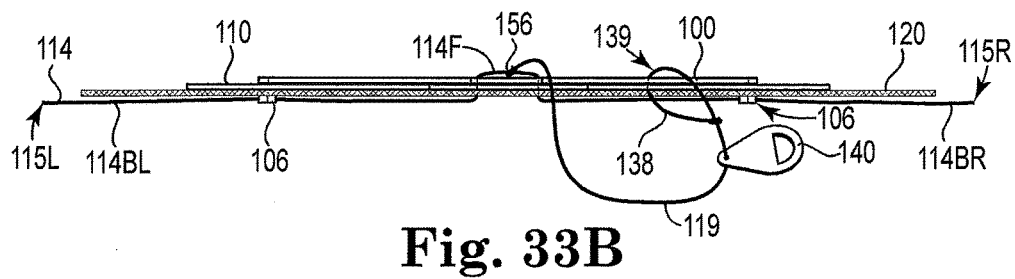
Figure 36A:
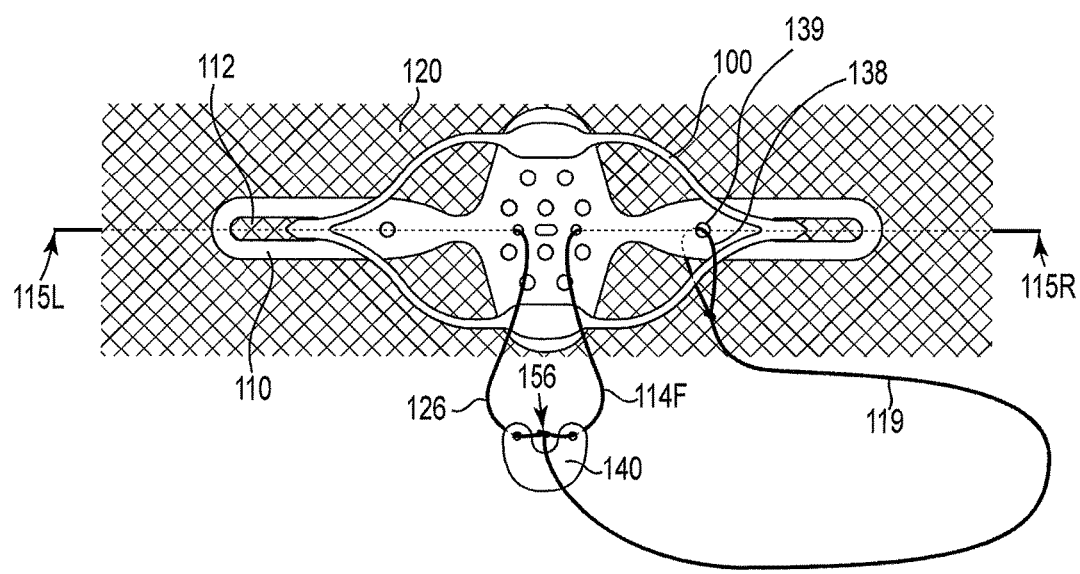
FIGS. 36A and 36B illustrate an embodiment of an implant.
Figure 36B:
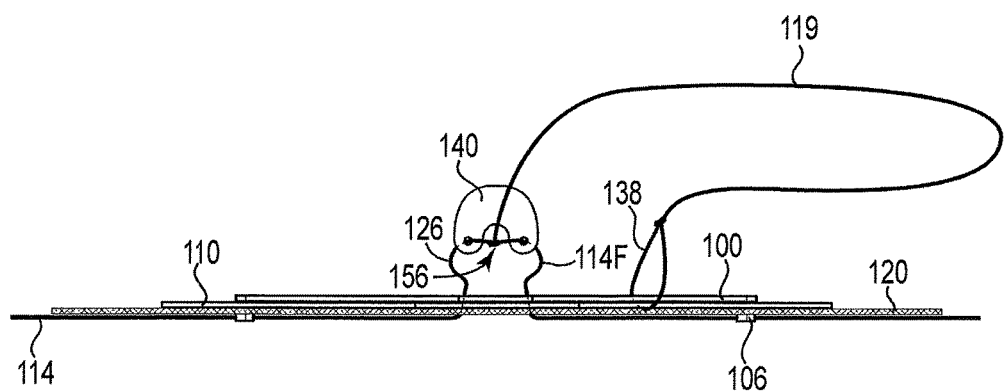

FIGS. 33A and 33B show a system that includes certain features in common with other system described herein as shown for example by commonly numbered features. Second tether (e.g., a connecting tether) 119 is attached at one end to tether 114 at a central location on front segment 114F by knot 156 (other attachment structures could also be useful such as adhesive). Front segment 114F extends across a front side of the implant between apertures 124L and 124R. The other end of second tether 119 is attached at loop 138 to backer 110 and indicator 100. Tab 140 is attached to second tether 119. Back segments 114BR and 114BL extend from a right or a left post 106 to ends 115R and 115L, respectively, and are of a length shorter than second tether 119. In use, tab 140 can be pulled to pull segments 114BR and 114BL through posts 106, releasing those segments from the posts. Segments 114BR and 114BL will become disengaged from the apertures of both posts 106 to release backer 110 and indicator 100 from material 120, while slack still remains in second tether 119. Thereafter, tab 140 can be pulled farther from the implant to remove the slack from second tether 119, then still farther to cause the aperture of tab 140 to engage knot 156. Drawing tab 140 still farther away from the implant will allow second tether 119 to carry backer 110 and indicator 100 away from implant material 120 and out of a patient. FIGS. 36A and 36B show a variant of the system of FIGS. 33A and 33B, including tab 140 that is attached through apertures in the tab to segment 114F, instead of second tether 119.

Figure 34A:
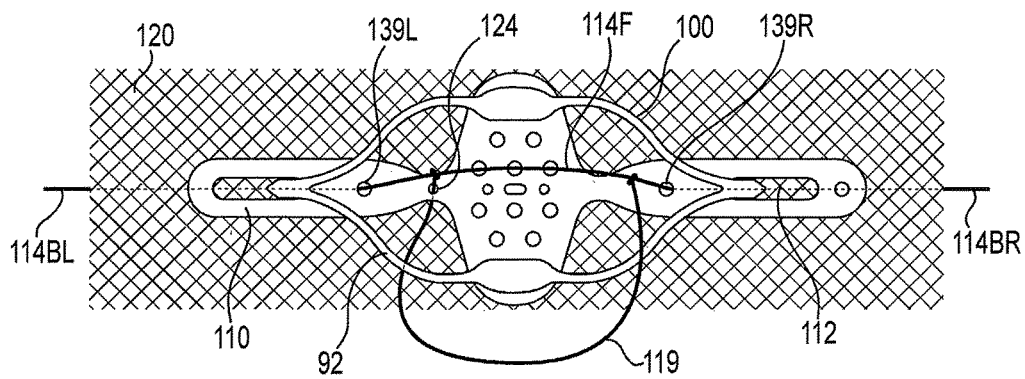
FIGS. 34A and 34B illustrate an embodiment of an implant.
Figure 34B:
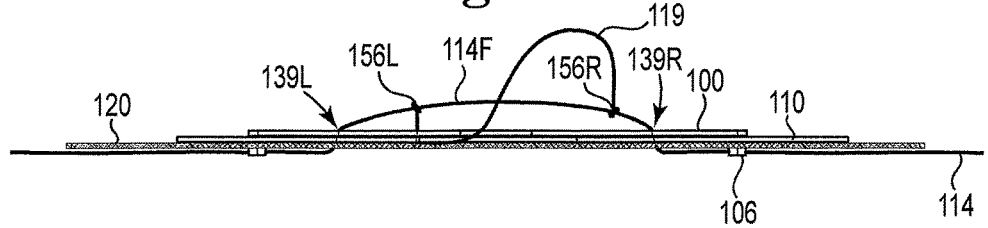

FIGS. 34A and 34B show a system that includes certain features in common with other systems described herein, as shown for example by commonly numbered features. Second tether 119 is attached at one end to front segment 114F by knot 156R (other attachment structures could also be useful such as adhesive) and to a second end to front segment 114F by knot 156L, near aperture 156L. Second suture 119, from knot 156L, extends through aperture 124 in backer 110 to the back or bottom side of backer 110 between backer 110 and implant material 120, then also below indicator 100 at bottom connector 92, so that second tether 119 forms a loop around both backer 110 and indicator 100. In use, second tether 119 or front segment 114 can be pulled to pull segments 114BR and 114BL through and out of apertures of posts 106, releasing those segments from the posts. Thereafter, second tether 119 or front segment 114 can be pulled farther from the implant to carry backer 110 and indicator 100 away from implant material 120 and out of a patient.

Figure 35A:
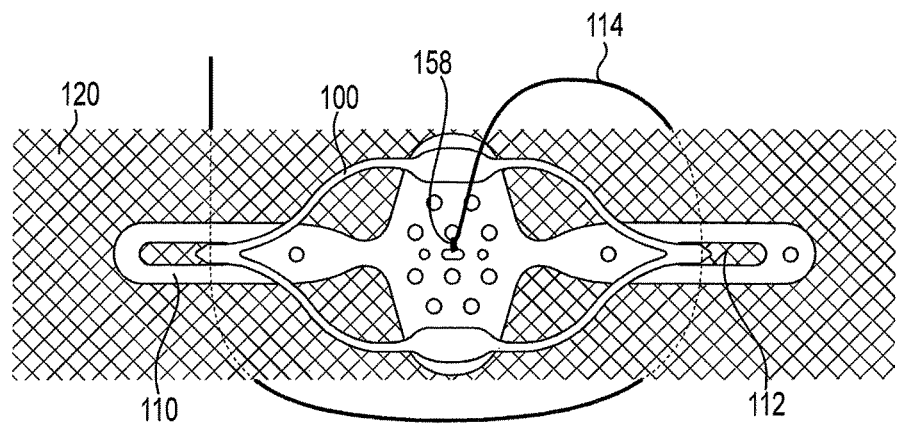
FIGS. 35A, 35B, 35C, and 35D illustrate embodiments of implants.
Figure 35B:
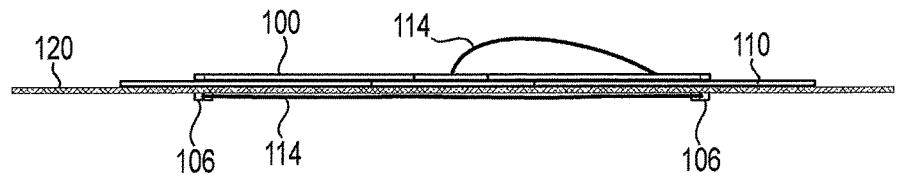

FIGS. 35A and 35B show a system that includes features in common with other system as described herein, as shown for example by commonly numbered features. Tether 114 of FIGS. 35A and 35B is attached at one end by knot 158 tied directly to backer 110 (other attachment devices or systems could alternately be used). Tether 114 then extends to the bottom side of implant material 120 and through two apertures, one each on posts 106. In use, tether 114 can be pulled away from the implant to release tether 114 from both posts 106, releasing that segment of the tether from the posts. Thereafter, tether 114 can be pulled farther from the implant to carry backer 110 and indicator 100 away from implant material 120 and out of a patient due to the attachment at knot 158. As illustrated, tether 114 is not attached to indicator 100, but can optionally be attached directly or indirectly to indicator 100.

Figure 35C:
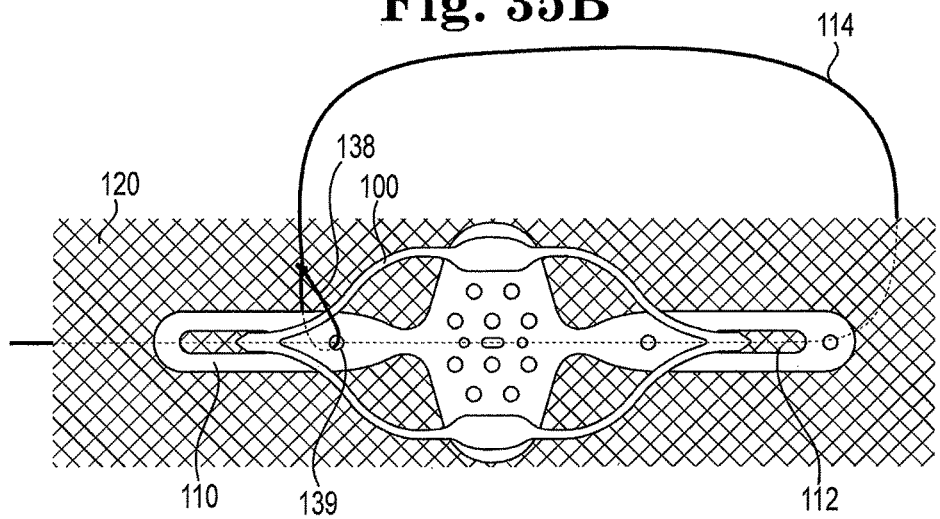
Figure 35D:
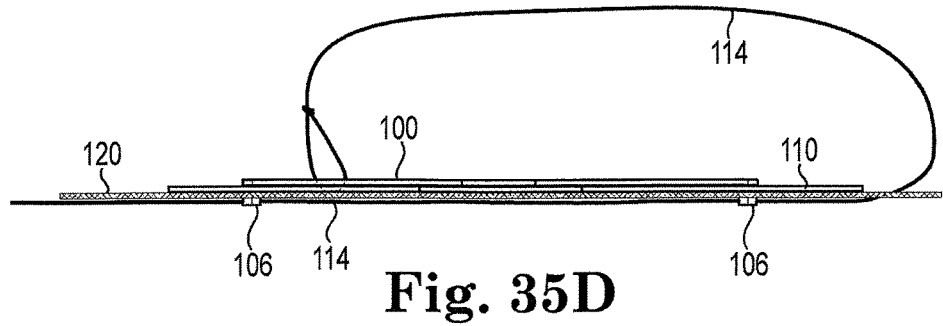

FIGS. 35C and 35D show systems that include features in common with other systems as described, as shown for example by commonly numbered features. Tether 114 of FIGS. 35C and 35D is attached at a first end by loop 139 extending around backer 110 and indicator 100 (other attachment devices or systems could alternately be used). Tether 114 extends from the attachment of the first end, to the bottom side of implant material 120, and through two apertures, one each on of posts 106. In use, tether 114 can be pulled away from the implant to release tether 114 from both posts 106, releasing that segment of the tether from the posts. Thereafter, tether 114 can be pulled farther from the implant to carry backer 110 and indicator 100 away from implant material 120 and out of a patient due to the attachment of loop 138 to backer 110 and indicator 100.

Figure 39A:
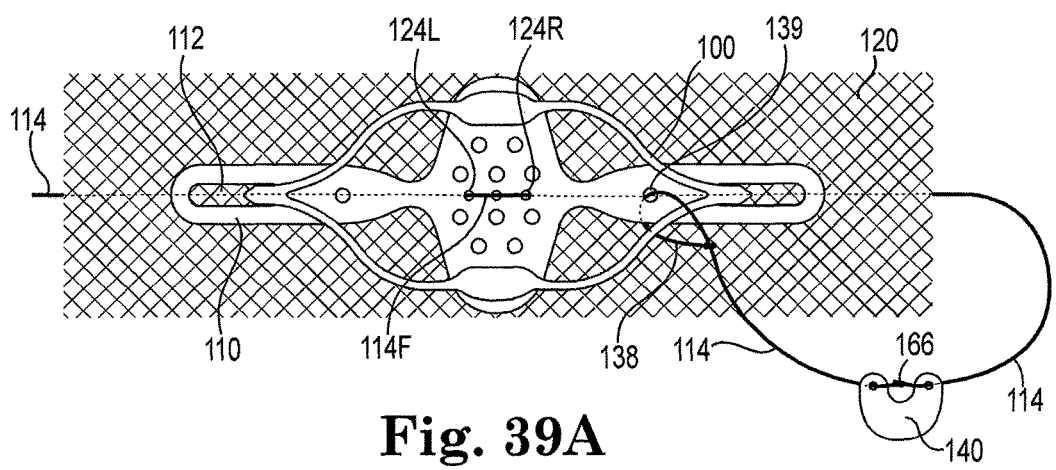
FIGS. 39A and 39B illustrate an embodiment of an implant.
Figure 39B:
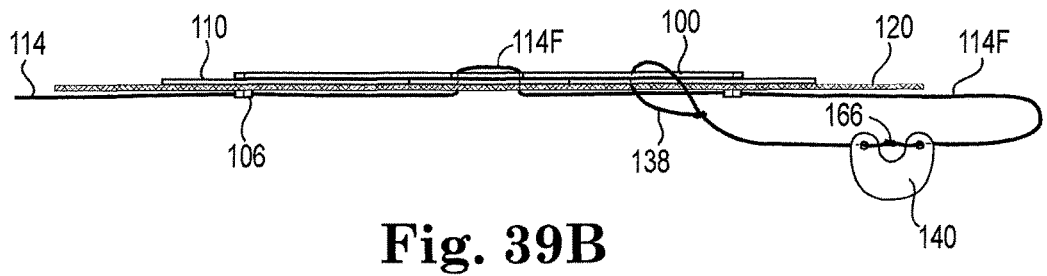

The system of FIGS. 39A and 39B includes features in common with FIGS. 35A, 35B, 35C, and 35D, and additionally a front segment of tether 114F that runs along the front side of the implant between apertures 124L and 124R. This front segment of tether 114F functions to hold backer 110 against implant material 120. An additional modified feature is tab 140, having two apertures of dimension smaller than a dimension of stopper (e.g., knot) 166. The apertures of tab 140 straddle stopper 166, causing tab 140 to remain in place adjacent to stopper 166.

Figure 37A:
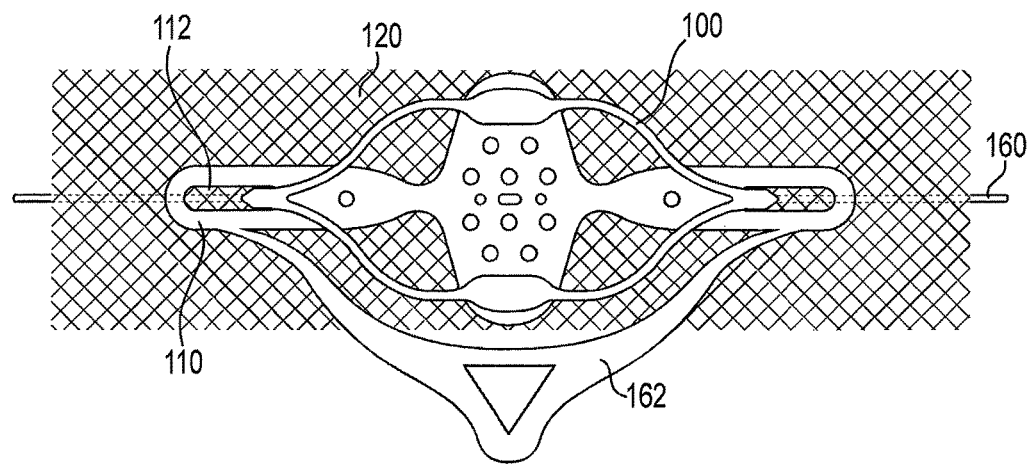
FIGS. 37A, 37B, 37C, and 37D illustrate embodiments of implants.
Figure 37B:
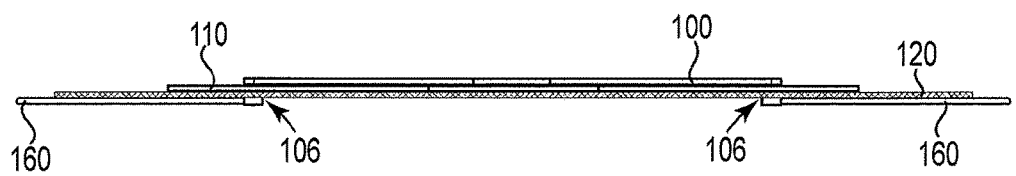
Figure 37C:
Figure 37D:
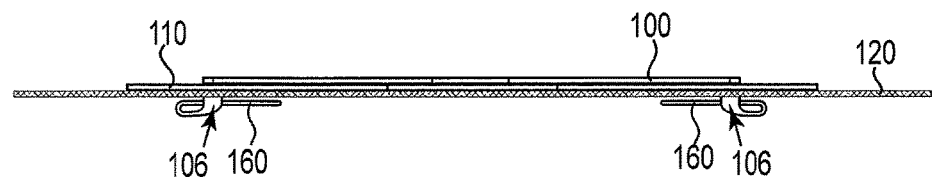

FIGS. 37A, 37B, 37C, 37D, 38A, and 38B show systems that include certain features in common with other systems as described, as shown for example by commonly numbered features. Different from other systems are the releasable fasteners shown at these figures. As shown at FIGS. 37A and 37B, releasable fastener 160 includes a flexible or malleable extension or "dogleg" connected to a distal end of a peg or post of indicator 100, instead of a pin-and-post configuration as shown in other embodiments. Releasable fastener 160 includes a post 106 as shown elsewhere, with extension or dogleg 160 extending in a length-wise direction away from a distal end of post 106 on a bottom side of implant material 120. Extension 160 can be flexible or malleable, e.g., made of polymer, metal or another suitable material for a surgical device. In use, backer 110 or indicator 100 can be pulled away from implant material 120 and extension 160 can deform or flex in a manner that allows each extension 160 to be pulled through implant material 120 from the back to the front side, then away from implant material 120 and out of the patient. FIG. 37A also shows handle 162, which can be used to grab backer 110 to pull backer 110 and indicator 100 away from implant material 120. FIG. 37D shows extension 160 (in this figure, e.g., a suture) curled back to be passed through an aperture of post 106.

Figure 38A:
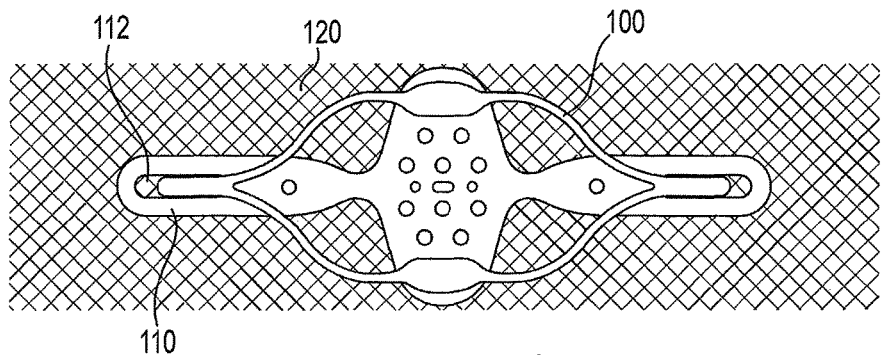
FIGS. 38A and 38B illustrate an embodiment of an implant.
Figure 38B:
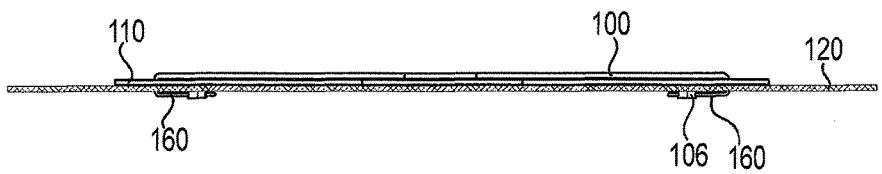

FIGS. 38A and 38B show posts 160, including an aperture at a distal end, and also show extension 160 (e.g., a suture) that extends from an end of indicator 100 on a front side, through implant material 120, then through the aperture at the distal end of post 106. During use, extension 160 can be removed from the aperture of post 106 and indicator 100 can be drawn away from implant material 120.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

The invention claimed is:

1. A pelvic surgical device comprising:
   an implant including a front side and a back side; and
   a tension indicator,
   the tension indicator having a first end, an opposing second end, and a length extending between the first end to the second end, the tension indicator being disposed on the front side of the implant, the tension indicator comprising:
      a first fastener secured to a first position of the implant, the first fastener including a post extending from the tension indicator located on the front side of the implant, the post extending through an aperture of the implant,
      a second fastener secured to a second position of the implant,
      a middle segment extending along a length between the first position and the second position, the middle segment including a flexible polymeric material, and
      a cursor located at the middle segment,
   wherein the cursor is configured to move in a first direction relative to a reference in response to a length of the implant between the first position and the second position increasing, and
   wherein the cursor is configured to move relative to the reference in a second direction opposite the first direction in response to the length of the implant between the first position and the second position decreasing.

2. The pelvic surgical device according to claim 1, wherein the tension indicator is configured to be removed from the implant.

3. The pelvic surgical device according to claim 1, further comprising a tether connected to the tension indicator.

4. The pelvic surgical device according to claim 1, wherein the reference is selected from:
   a marking on the implant,
   a feature of the tension indicator, and
   a feature of a backer located between the front side of the implant and the tension indicator.

5. The pelvic surgical device according to claim 1, wherein the reference is located on a backer located between the front side of the implant and the tension indicator, and the backer is configured to be removed from the implant.

6. The pelvic surgical device according to claim 1, wherein
the post comprises a distal end comprising an expanded head, the post being held at the aperture by the expanded head, the post configured to be removed from the aperture by manually passing the expanded head through the aperture.

7. The pelvic surgical device according to claim 6, further comprising a backer disposed between the tension indicator and the front side of the implant, wherein the post extends through a backer aperture, and a tether is connected to the tension indicator and the backer on the front side of the implant.

8. The pelvic surgical device according to claim 1, wherein the middle segment comprises an upper connector, a lower connector, and an opening between the upper connector and the lower connector.

9. The pelvic surgical device according to claim 8, wherein the upper connector configured to move toward the lower connector in response to the implant being lengthened.

10. The pelvic surgical device according to claim 8, wherein one or more of the upper connector and the lower connector comprises a spring segment that lengthens as the tension indicator is lengthened from an original state, and that returns to a unlengthened state as the tension indicator returns to the original state.

11. The pelvic surgical device according to claim 1, wherein the implant is a urethral sling comprising:
an extensible mesh comprising a tissue support portion and two extension portions extending away from the tissue support portion; and
two self-fixating tips, one at an end of each extension portion,
wherein the urethral sling has a length between the two ends and a midpoint along the length, and the tension indicator is located against the front surface of the implant that includes the midpoint.

12. A pelvic surgical device comprising:
an extensible strip having a front side and a back side;
a tension indicator having a first end, an opposing second end, and a length extending between the first end to the second end along the front side of the strip;
a backer located between the tension indicator and the front side of the extensible strip; and
a tether connected to the tension indicator, and the backer.

13. The pelvic surgical device according to claim 12, wherein
a first segment of the tether secures the tension indicator to the implant at a fastener,
a second segment of the tether is connected to the tension indicator and the backer,
wherein pulling a location of the tether a first distance away from the implant releases the fastener, while slack remains in the second segment, and
wherein pulling the location of the tether an added distance removes the slack, and then removes the tension indicator, the backer, or the tension indicator and the backer, from the patient.

14. The pelvic surgical device according to claim 13, wherein the tension indicator further comprises:
the first end comprising a first fastener,
the second end comprising a second fastener,
a middle segment disposed between the first end and the second end, the middle segment comprising an upper connector, a lower connector, and an opening between the upper connector and the lower connector,
wherein the backer is viewable at the opening.

15. The pelvic surgical device according to claim 14, wherein when the implant is lengthened, the backer is not lengthened, and the tension indicator is lengthened, and the upper connector moves relative to the backer.

16. A method of placing the pelvic surgical device of claim 1 in a body of a patient, the method comprising:
placing the pelvic surgical device in the patient while positioning the implant to support tissue;
viewing the tension indicator and
adjusting a tension of the implant.

17. The method according to claim 16, further comprising removing the tension indicator from the implant and the patient while the implant remains implanted in the patient.

18. A method of treating urinary incontinence, comprising:
providing the pelvic surgical device according to claim 1;
creating a medial incision in a male or female patient;
dissecting from the medial incision to tissue below a urethra;
placing the implant at a location to support the urethra;
placing a first end of the implant along a tissue path extending from below the urethra toward a first obturator foramen of the patient;
placing a second end of the implant along a tissue path extending from below the urethra toward a second obturator foramen of the patient;
viewing the tension indicator;
releasing the tension indicator from the implant; and
removing the tension indicator from the patient.

* * * * *